(12) United States Patent
Hyde et al.

(10) Patent No.: US 11,383,051 B2
(45) Date of Patent: Jul. 12, 2022

(54) COLLAPSIBLE, DISPOSABLE MEDICATION INHALATION SPACER AND METHOD

(71) Applicant: THAYER MEDICAL CORPORATION, Tucson, AZ (US)

(72) Inventors: Joel Hyde, Tucson, AZ (US); Jennifer Johnson, Tucson, AZ (US)

( * ) Notice: Subject to any disclaimer, the term of this patent is extended or adjusted under 35 U.S.C. 154(b) by 229 days.

(21) Appl. No.: 16/777,529

(22) Filed: Jan. 30, 2020

(65) Prior Publication Data

US 2020/0306465 A1 Oct. 1, 2020

Related U.S. Application Data

(63) Continuation-in-part of application No. 16/368,581, filed on Mar. 28, 2019.

(51) Int. Cl.
*A61M 15/00* (2006.01)

(52) U.S. Cl.
CPC ...... *A61M 15/0016* (2014.02); *A61M 15/009* (2013.01); *A61M 15/0018* (2014.02); *A61M 15/0021* (2014.02)

(58) Field of Classification Search
CPC ...... A61M 11/00; A61M 11/02; A61M 11/06; A61M 11/08; A61M 15/00; A61M 15/0013; A61M 15/0016; A61M 15/0018; A61M 15/0021; A61M 15/0086–0088; A61M 15/009

See application file for complete search history.

(56) References Cited

U.S. PATENT DOCUMENTS

| 4,951,661 A | 8/1990 | Sladek | 128/202.27 |
| 4,953,545 A | 9/1990 | McCarty | 128/200.23 |
| D335,175 S | 4/1993 | Sladek | D24/110 |

(Continued)

FOREIGN PATENT DOCUMENTS

| CA | 2212642 | 8/1996 | A63B 23/18 |
| CA | 2223518 | 12/1996 | A63B 23/18 |

(Continued)

OTHER PUBLICATIONS

International Search Report and Written Opinion issued in related PCT International Patent Application Serial No. PCT/US20/25714, dated Aug. 12, 2020 (14 pages).

(Continued)

*Primary Examiner* — Rachel T Sippel
(74) *Attorney, Agent, or Firm* — Hayes Soloway P.C.

(57) ABSTRACT

A medication inhalation apparatus includes an outer housing, movable between collapsed and expanded states, encompassing a first volume. An inner housing within the outer housing encompasses an inner volume. An inhaler opening to the first volume is within a wall of the outer housing at a first location. A mouth opening to the inner volume is within a wall of the outer housing and the inner housing at a second location. A one-way inhalation valve connecting the first volume and the inner volume is within a wall of the inner housing. A one-way exhalation valve connecting the inner volume and the exterior of the outer housing is within a wall of the outer housing and inner housing at a third location. In the expanded state, gas flows from the inhaler to the first volume, the first volume to the inner volume, and the inner volume to a user's mouth.

17 Claims, 17 Drawing Sheets

(56) References Cited

U.S. PATENT DOCUMENTS

| | | | |
|---|---|---|---|
| 5,427,089 A | 6/1995 | Kraemer | A61M 11/00 |
| D362,500 S | 9/1995 | Cook et al. | D24/110 |
| 5,474,058 A | 12/1995 | Lix | 128/200.18 |
| 6,014,972 A | 1/2000 | Sladek | 128/203.12 |
| 6,039,042 A | 3/2000 | Sladek | A61M 11/00 |
| 6,098,619 A | 8/2000 | Britto | A61M 11/003 |
| 6,202,643 B1 | 3/2001 | Sladek | 128/200.23 |
| 6,435,176 B1 | 8/2002 | Berg et al. | 128/200.23 |
| 6,463,929 B1 | 10/2002 | Scheuch | A61M 15/00 |
| 6,550,473 B1 | 4/2003 | Sladek | 128/200.23 |
| 6,679,252 B2 | 1/2004 | Sladek | 128/200.23 |
| 7,347,203 B2 | 3/2008 | Marler et al. | 128/201.13 |
| 7,360,537 B2 | 4/2008 | Snyder et al. | 128/200.23 |
| 7,921,846 B1 | 4/2011 | Marler et al. | 128/205.24 |
| 2002/0129814 A1 | 9/2002 | Sladek | A61M 11/00 |
| 2009/0032019 A1 | 2/2009 | Green | A61M 16/10 |
| 2010/0163045 A1 | 7/2010 | Powell | A61M 11/00 |
| 2013/0276781 A1* | 10/2013 | Steelman | A61M 15/0023 128/203.12 |
| 2016/0045686 A1 | 2/2016 | Jaroslavsky | A61M 15/0088 |
| 2019/0151578 A1 | 5/2019 | Dennis | A61M 15/0088 |
| 2019/0231994 A1 | 8/2019 | Jaroslavsky | A61M 15/0086 |
| 2019/0358415 A1 | 11/2019 | Taghavi | A61M 15/0021 |
| 2020/0282158 A1 | 9/2020 | Friel | A61M 15/0086 |

FOREIGN PATENT DOCUMENTS

| | | | |
|---|---|---|---|
| EP | 1204437 | 2/2005 | A61M 11/04 |
| WO | WO 96/37249 | 11/1996 | A61M 15/00 |
| WO | WO 2017205907 | 12/2017 | A61M 15/00 |
| WO | WO2017205907 | 12/2017 | A61M 15/00 |
| WO | WO2019007968 | 1/2019 | A61M 15/00 |

OTHER PUBLICATIONS

Invitation to Pay Additional Fees issued in related PCT International Patent Application Serial No. PCT/US20/25714, dated Jun. 17, 2020 (2 pages).

U.S. Appl. No. 16/368,581, filed Mar. 28, 2019.

U.S. Appl. No. 16/368,585, filed Mar. 28, 2019.

Australian Certificate of Registration of Trademark, No. 1751570 for Liteaire, filed Feb. 10, 2016 (1 pg).

LiteAire® sales literature, downloaded from http://thayermedical.com on Apr. 18, 2019 (20 pgs).

Notice of Allowance issued in U.S. Appl. No. 16/368,585, dated Nov. 14, 2019 (9 pgs).

Office Action issued in U.S. Appl. No. 16/368,585, dated Jul. 31, 2019 (16 pgs).

Office Action issued in related co-pending U.S. Appl. No. 16/368,581, dated Apr. 19, 2021, 10 pgs.

International Preliminary Report on Patentability issued in related PCT International Patent Application Serial No. PCT/US20/25714, dated Oct. 7, 2021 (11 pages).

* cited by examiner

Method of expanding a medication inhalation apparatus from an initially flat, collapsed state — 600

610 — Providing, in the collapsed state, an outer housing, an inner housing positioned within the outer housing, wherein the outer housing and the inner housing are substantially airtight when expanded, an inhaler opening formed at least partially within a sidewall of the outer housing at a first location, a mouth opening positioned within a sidewall of the outer housing and the inner housing at a second location, a one-way inhalation valve positioned within a sidewall of the inner housing, and a one-way exhalation valve positioned within a sidewall of the outer housing and the inner housing at a third location;

620 — Pressing a pair of opposite sidewall panels on the outer housing;

630 — Manually expanding the outer housing and inner housing to create a first volume encompassed by the outer housing and an inner volume encompassed by the inner housing, wherein the inhaler opening is in fluid communication with the first volume, wherein the mouth opening is in fluid communication with the inner volume, wherein the inhalation valve connects the first volume and the inner volume, wherein the exhalation valve connects the inner volume and the exterior of the outer housing, and wherein gas is flowable from the metered dose inhaler to the first volume, from the first volume to the inner volume, and from the inner volume to the mouth of a patient.

FIG. 6

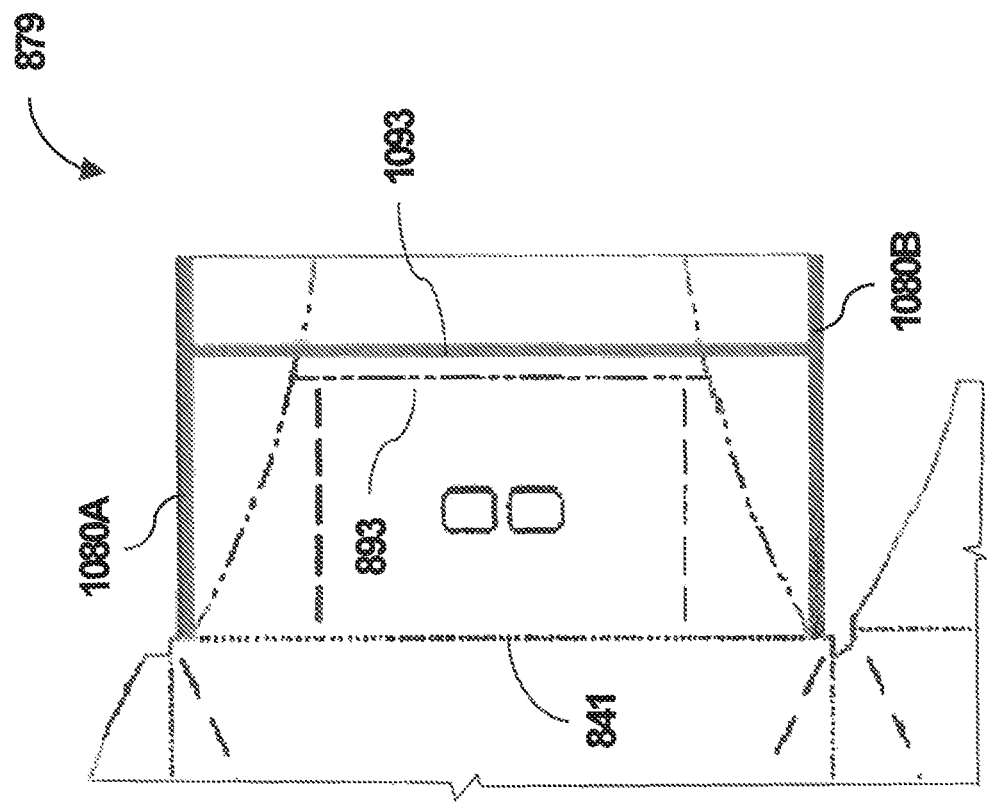

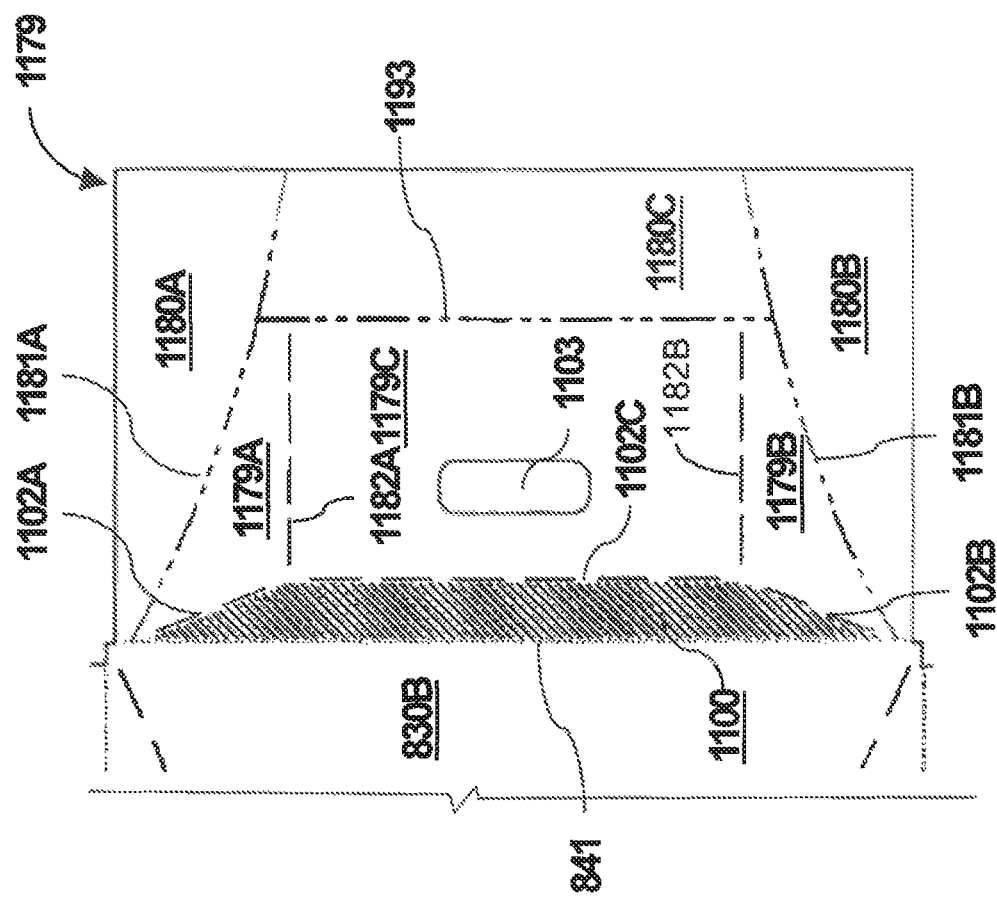

ered to as a "valved holding chamber" or "VHC".

COLLAPSIBLE, DISPOSABLE MEDICATION INHALATION SPACER AND METHOD

CROSS REFERENCE TO RELATED APPLICATION

This application is a continuation-in-part of co-pending U.S. patent application Ser. No. 16/368,581, filed Mar. 28, 2019, the contents of which are incorporated herein by reference.

FIELD OF THE DISCLOSURE

The present disclosure is generally related to aerosol medication inhalers and more particularly is related to valved chambers for delivering aerosol medication from an MDI canister.

BACKGROUND OF THE DISCLOSURE

Pressurized Metered Dose Inhaler (MDI) canisters, which have been used since 1956, ordinarily are sold with a dispenser or so-called "boot" that includes an actuator, a nozzle, and a mouthpiece. The user can self-administer the MDI medicament using the boot alone; however, the user must place the mouthpiece of the boot in or near his/her mouth and inhale at essentially the same time the MDI canister is actuated. Some users, like young children and the elderly, find it difficult to coordinate their inhalation with the actuation of the MDI, and even if the user is able to coordinate their inhalation with MDI inhalation, a lot of medicament is deposited into the oropharynx, leading to undesirable side-effects, such as hoarseness or thrush when using corticosteroids.

At first, "Spacers" were created to address the undesirable oropharyngeal deposition; however, these devices do not address the need for coordinated breathing technique. Medical device manufacturers have since created valved holding chambers (VHCs) to address both issues. To combat oropharyngeal deposition, VHCs (like spacers) have a chamber that holds the aerosol plume. This chamber lets the aerosol plume decelerate giving medicament particles the volume needed to aerosolize, and it allows particles that would normally impact on the user's oropharynx to deposit on the inside of the chamber instead. To help alleviate issues with the synchronization of a user's breath with MDI actuation, VHCs also employ a valving system that permits the user's inhalation to draw the medicament from the chamber but re-directs the user's exhalation to be vented out of the mouthpiece of the VHC such that the remaining aerosolized medicament inside the chamber is not blown backwards out of the chamber. This allows patients who can't synchronize their inhalation with MDI actuation to get a significant dose of medicament. It also allows the patient to continue breathing through the VHC throughout the treatment, as the presence of the exhalation valve means there is no need to remove the VHC from the patient's mouth during exhalation. Ultimately, the patient can take in the full dose, while breathing as normally as possible, over multiple breaths if necessary. These devices have now become the recommended as the best-practice accessory to an MDI for patients of all ages.

Many commercially available VHCs, like the Aerochamber Plus® Z-Stat® device available from Monaghan Medical Corporation, and Optichamber® Diamond device available from Philips Respironics, are made of rigid plastic and are substantially cylindrical in shape with a diameter of a couple inches and a length of roughly half a foot, which presents problems to users that need to carry MDI canisters with them all day in case of an emergency asthma attack. Also, in facilities that store large numbers of holding chambers, like hospitals or spirometry testing facilities, the cylindrical shape of most VHCs means that the storage of many VHCs takes up a significant amount of space. Some VHC manufacturers have identified these issues and have partially addressed them by creating collapsible cylindrical VHCs. Many of these collapsible VHCs, however, don't offer a significant advantage to a non-collapsible chamber. For example, the BreatheRite™ collapsible device available from Medline Industries, Inc., shortens the length of the device by a couple inches when collapsed, but the device is still a rigid cylinder with the same diameter. The cylindrical shape still means that the device can't fit comfortably in a user's pocket, as well as meaning that storing large quantities of these devices would still take large amounts of space. The Thayer Medical LiteAire® spacer device collapses to a substantially flat configuration and the dimensions of the VHC allow the device to be carried unobtrusively in a shirt pocket or purse. Also, many LiteAire® spacer devices can be stored in a relatively small area because the packaged devices can be stacked flat on top of each other with very little empty space between devices, which is not possible with cylindrically shaped devices like the BreatheRite™ collapsible device.

Conventional VHCs, like the Aerochamber Plus® Z-Stat® device and Optichamber® Diamond device, cost in the range of $10-20. Some medical applications, like spirometry testing, only require a VHC to be used during a brief testing period by a patient, and this price offers a barrier to the use of a VHC in these settings. While lower cost plastic VHCs have recently been introduced to the market, the recent awareness of the need for environmental sustainability identified another problem with the rigid cylindrical plastic solution. Plastic taxes the environment when disposed of with the frequency required in higher-usage clinical environments like spirometry testing facilities. The LiteAire® offers a solution to this problem as well, with 98% of the device being made from paperboard, the environmental impact upon disposal of the device is substantially reduced.

Another benefit of the LiteAire®'s collapsible device construction is that the device is made of a paperboard which is inherently an antistatic material. The fact that the traditional plastic construction of other VHCs creates a large amount of medicament deposition due to static build up on the inside surface of the VHC has been established by multiple sources, including some patents. Multiple patents have been filed for VHCs or spacers made from antistatic materials. For example, U.S. Pat. Nos. 6,435,176 and 7,360,537, which describe devices made from metal and antistatic plastic, respectively, seek to address this problem. These patents offer solutions to electrostatic deposition but run into some of the same rigidity, cost, and disposal problems mentioned above; and they remain bulky and/or expensive. The LiteAire® collapsible device is able to reduce electrostatic deposition as well as being inexpensive, easily portable and environmentally friendly.

While the LiteAire already offers an inexpensive, disposable, collapsible, and antistatic VHC, additional features are still possible. The current iteration of the LiteAire requires the user or caregiver to pinch the sides of the barrier wall during the process of administering the dose of medicament. Anytime a use detail such as this is conveyed in the instructions (also known as a labeling control), if it can affect dose delivery, a design control is preferred. The more intended and reproducible medicament delivery is dependent upon the device design (not on the user), the better.

Further advantage can be gained by achieving near totality of the separation between the chamber holding the aerosolized medicament and the mouthpiece section without the assistance of the user's "pinch". As such, a redesign of the mouthpiece configuration can do away with any holding requirement for the user by disabling any effect the user's exhaled breath might otherwise have on aerosol plume in the chamber.

The present application addresses these potential variants in the LiteAire design. These variants would continue to provide the same advantages that the LiteAire already offers over the prior art discussed above and would supplement those advantages.

SUMMARY OF THE DISCLOSURE

Accordingly, it is an object of the invention to improve the efficiency of a collapsible/expandable valved chamber device for delivering MDI medications for the like.

It is another object of the invention to reduce the amount of MDI medication lost from a user exhaling into the chamber by preventing a user using a collapsible/expandable valved chamber from inadvertently blowing MDI medication out of the collapsible/expandable valved chamber if the user inadvertently exhales while actuating an MDI canister that introduces the medication into the collapsible/expandable valved chamber, or the user takes in the dose over multiple breaths.

It is another object of the invention to provide an inexpensive, disposable, collapsible valved chamber for delivering MDI medications or other inhaled treatments.

It is another object of the invention to provide an inexpensive, disposable valved chamber which is collapsible to a flat configuration.

It is another object of the invention to provide a valved chamber which is sufficiently inexpensive that it can be used as a discardable diagnostic dosing aid, temporary medication delivery aid, or training aid by means of which a health care provider can demonstrate proper techniques for using a permanent valved chamber.

It is another object of the invention to provide a valved chamber which can pop up from a collapsed configuration to an expanded configuration ready for use.

It is another object of the invention to provide a valved chamber which can pop up from a collapsed configuration to an expanded configuration ready for use and retain the expanded configuration.

It is another object of the invention to provide a valved chamber which can be "popped up" or erected from a collapsed configuration by a user with a minimal amount of effort.

The present disclosure can be viewed as providing a medication inhalation apparatus. Briefly described, in architecture, one embodiment of the system, among others, can be implemented as follows. The apparatus includes an outer housing collapsible into a substantially flat configuration and expandable to bound a first volume adapted to receive a plume of medication particles ejected by an MDI inhaler.

The apparatus also includes a fully contained inner housing also collapsible into a substantially flat configuration, located within the outer housing and expandable to bound a second volume. A first opening is formed through a wall of the outer housing at a first location, in fluid communication with the first volume, and adapted to accommodate a mouthpiece of an MDI inhaler. Second and third openings are formed through walls of the outer housing and the inner housing adapted to form an user mouth opening in fluid communication with the second volume. A one-way inhalation valve is located within a wall of the inner housing. The inhalation valve connects the first volume and the second volume. A one-way exhalation valve is located within a wall of the outer housing and the inner housing. The exhalation valve connects the inner volume and the exterior of the outer housing. When the apparatus is in an expanded state, gas is flowable from a connected MDI to the first volume, from the first volume to the second volume, and from the inner volume to the mouth of a user.

The present disclosure can also be viewed as providing methods of expanding a medication inhalation apparatus from an initially flat, collapsed state to an expanded state by providing a medication inhalation apparatus as above described, and manually pressing a pair of opposite sidewall panels on the outer housing towards one another, whereby to force the opposite sidewall panels into positions approximately perpendicular to top and bottom panels of the outer housing, and inserting a mouthpiece of an MDI inhaler into an inhaler opening in the outer housing, whereupon the apparatus is ready for use by a patient.

The present disclosure can also be viewed as providing a medication inhalation apparatus. Briefly described, in architecture, one embodiment of the apparatus, among others, can be implemented as follows. The apparatus includes an outer housing, collapsible into a substantially flat configuration and expandable to bound a first volume adapted to receive a plume of medication particles ejected by an MDI inhaler. An inner flap is located within the outer housing and, together with the outer housing, is expandable to bound a second volume within the outer housing. A first opening is formed through a wall of the outer housing at a first location. The first opening is in fluid communication with the first volume, and is adapted to accommodate a mouthpiece of an MDI inhaler. A second opening is formed through a wall of the outer housing at a second location. The second opening is adapted to fbrm a user mouth opening in fluid communication with the second volume. A one-way inhalation valve is located within the inner flap, the inhalation valve connecting the first volume and the second volume. A one-way exhalation valve is located within a wall of the outer housing, the exhalation valve connecting the second volume and an exterior of the outer housing. In an expanded state, gas is flowable from a connected MDI to the first volume, from the first volume to the second volume, and from the second volume to the mouth of a user.

In one aspect of the apparatus, the outer housing and the inner flap are constructed from a single piece of stock. In a particular aspect of the apparatus, the inner flap is connected to the outer housing at a fold. In another particular aspect of the apparatus, the single piece is sheet stock, and the outer housing and the inner flap are formed by folding the sheet. In another particular aspect, the outer housing is connected to the inner flap adjacent the mouth opening side of the sheet stock. In another particular aspect, at least two corners on a bottom panel of the outer housing are receded corners.

In another aspect of the apparatus, the outer housing and the inner housing are at least partially constructed from antistatic material.

In another aspect of the apparatus, the inner flap comprises a plurality of panels having a plurality of tension relief lines.

In another aspect of the apparatus, the inner flap is adhesively attached to a bottom panel of the outer housing along at least three adhesive lines.

In another aspect of the apparatus, the inner flap comprises an adhesive panel adjacent to a top panel of the outer housing, wherein the adhesive panel is adhesively attached to the top panel of the outer housing. In a particular aspect, the adhesive panel extends substantially across a width of the inner flap.

The present disclosure can also be viewed as providing a medication inhalation apparatus. Briefly described, in architecture, one embodiment of the apparatus, among others, can be implemented as follows. The apparatus includes an outer housing, collapsible into a substantially flat configuration and expandable to bound a first volume adapted to receive a plume of medication particles ejected by an MDI inhaler. An inner flap is located within the outer housing and is expandable to bound a second volume within the outer housing. An edge panel of the inner flap is adhesively affixed to a portion of the outer housing to secure the second volume. A first opening is formed through a wall of the outer housing at a first location. The first opening is in fluid communication with the first volume and is adapted to accommodate a mouthpiece of an MDI inhaler. A second opening is formed through a wall of the outer housing at a second location and is adapted to form a user mouth opening in fluid communication with the second volume. A one-way inhalation valve is located within a central panel of the inner flap, the inhalation valve connecting the first volume and the second volume. A one-way exhalation valve is located within an outer panel of the inner flap and a wall of the outer housing, the exhalation valve connecting the second volume and an exterior of the outer housing. In an expanded state, gas is flowable from a connected MDI to the first volume, from the first volume to the second volume, and from the second volume to the mouth of a user.

In one aspect of the apparatus, the outer housing and the inner flap are constructed from a single piece of stock. In a particular aspect of the apparatus, the inner flap is connected to the outer housing at a fold. In another particular aspect of the apparatus, the single piece is sheet stock, and the outer housing and the inner flap are formed by folding the sheet. In another particular aspect, the outer housing is connected to the inner flap adjacent the mouth opening side of the sheet stock.

In another aspect of the apparatus, the outer housing and the inner housing are at least partially constructed from antistatic material.

In another aspect of the apparatus, the one-way exhalation valve comprises an exhalation valve located within the inner flap and a valve opening located within a wall of the outer housing.

The present disclosure can also be viewed as providing methods of expanding a medication inhalation apparatus from an initially flat, collapsed state to an expanded state. In this regard, one embodiment of such a method, among others, can be broadly summarized by the following steps: providing, in the collapsed state, an outer housing, an inner flap located within the outer housing, wherein the outer housing and the inner flap are substantially airtight when expanded, an inhaler opening formed at least partially within a sidewall of the outer housing at a first location, a mouth opening positioned within a sidewall of the outer housing at a second location, a one-way inhalation valve positioned within a sidewall of the inner flap, and a one-way exhalation valve positioned within a sidewall of the outer housing at a third location; pressing a pair of opposite sidewall panels on the outer housing; and manually expanding the outer housing and inner flap to create a first volume encompassed by the outer housing and a second volume encompassed by the inner flap and the outer housing, wherein the inhaler opening is in fluid communication with the first volume, wherein the mouth opening is in fluid communication with the second volume, wherein the inhalation valve connects the first volume and the second volume, wherein the exhalation valve connects the second volume and the exterior of the outer housing, and wherein gas is flowable from the inhaler to the first volume, from the first volume to the second volume, and from the second volume to the mouth of a patient.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 6 is a flowchart describing a method of expanding a medication inhalation apparatus from an initially flat, collapsed state, in accordance with a first embodiment of the present disclosure.

FIG. 10 is a close-up plan view of a glue pattern of the inner flap shown in FIG. 8B, in accordance with the fourth exemplary embodiment of the present disclosure.

FIG. 11 is a close-up plan view of an inner flap for use in conjunction with the sheet shown in FIG. 8A, in accordance with a fifth exemplary embodiment of the present disclosure.

DETAILED DESCRIPTION

Figure 1A:
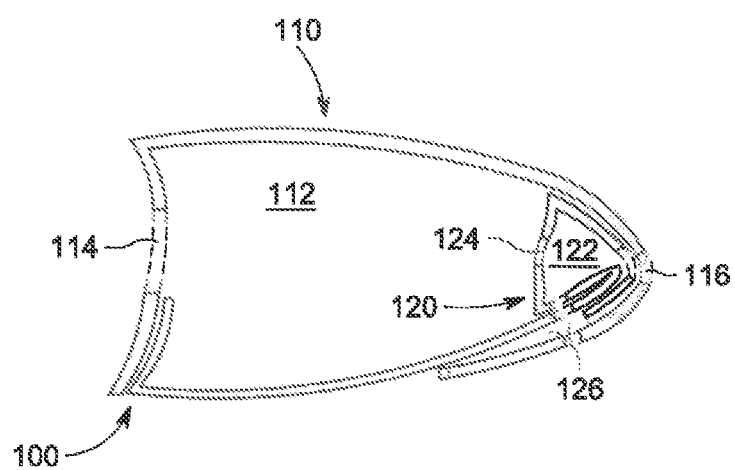
FIG. 1A is a longitudinal cross-sectional view of the apparatus in an expanded state, in accordance with a first exemplary embodiment of the present disclosure.

FIG. 1A is a longitudinal cross-sectional view of the apparatus 100 in an expanded state, in accordance with a first exemplary embodiment of the present disclosure. The apparatus 100 includes an outer housing 110, movable between a collapsed state and an expanded state. The collapsed state has a substantially flat configuration. The expanded state encompasses a first volume 112. The apparatus also includes an inner housing 120 positioned within the outer housing 110 and encompassing an inner volume 122. Housing 110 has perforations on the side and openings on the side that render it not airtight. Housing 120 has holes at the corners. The interface between volume 122 and 112 is the substantially airtight portion.

An inhaler opening 114 is formed at least partially within a sidewall of the outer housing 110 at a first location. The inhaler opening 114 is in fluid communication with the first volume 112, and the mouthpiece of a metered dose inhaler (see FIG. 3) can be inserted within the inhaler opening 114. A mouth opening 116 is positioned within a sidewall of the outer housing 110 and the inner housing 120 at a second location. The mouth opening 116 is in fluid communication with the inner volume 122. A one-way inhalation valve 124 is positioned within a sidewall of the inner housing 120. The inhalation valve 124 connects the first volume 112 and the inner volume 122. A one-way exhalation valve 126 is positioned within a sidewall of the outer housing 110 and the inner housing 120 at a third location. The exhalation valve 126 connects the inner volume 122 and the exterior of the outer housing 110. When the apparatus 100 is in an expanded state, gas is flowable from the metered dose inhaler to the first volume 112, from the first volume 112 to the inner volume 122, and from the inner volume 122 to the mouth of a user. In the expanded state, gas is also flowable from the mouth of a user to the inner volume 122 and to the exterior of the outer housing 110.

Figure 1B:
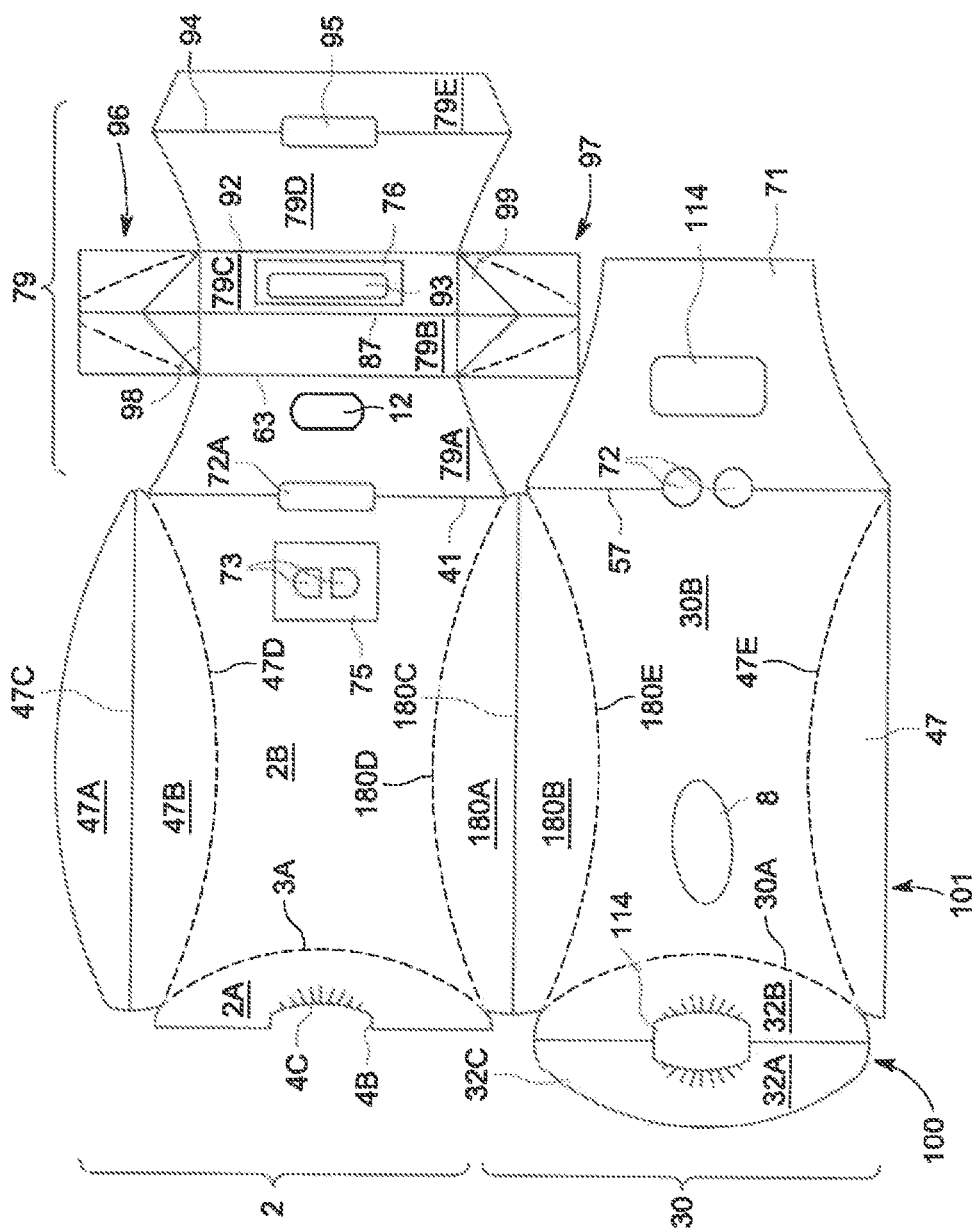
FIG. 1B is a plan view of a sheet from which the apparatus is constructed, in accordance with a first exemplary embodiment of the present disclosure.

FIG. 1B is a plan view of a sheet 101 from which the apparatus 100 is constructed, in accordance with a first exemplary embodiment of the present disclosure. The sheet 101, when assembled, pops up into the expanded state shown in FIG. 1A. FIG. 1B shows the exterior side of the sheet 101, i.e., the side that forms the exterior of the apparatus 100 as assembled. Sheet 101 includes a bottom section 2, a top section 30, an inner housing section 79, and an outer mouthpiece section 71. The inner housing 120 is formed from the panels in the inner housing section 79, while the outer housing 110 is formed from the remaining portions of the sheet 101. The bottom section 2 and top section 30 are connected by a right side section, which includes two right side panels 180A and 180B connected by a straight scored fold line 180C as shown. Right side panel 180A is connected along an arcuate "skip-scored" or perforated fold line 180D to bottom panel 2B, and right side panel 180B is connected along an arcuate skip-scored fold line 180E to top panel 30B. (A skip-scored fold line includes a sequence of scored and non-scored sections of a fold line having the appearance of dashed line.).

On the top section 30, adhesive attachment panel 47 is connected by an arcuate scored or perforated fold line 47E to top panel 30B, and eventually is adhesively attached to the inner surface of left side panel 47A on bottom section 2. Left side panel 47A is connected to panel 47B, which is connected to bottom panel 2B by arcuate fold line 47D.

In one example, top panel 30B may have a window opening 8 therein, with a piece of transparent membrane adhesively attached to the inner surface of top panel 30B source to provide a sealed, transparent window into the interior of valved chamber 1A. In another example, the apparatus 100 may have no viewing window.

On the bottom section 2, the rear end portion of bottom panel 2B is connected along an arcuate skip-scored fold line 3A to an inner boot adapter panel 2A. Conversely, on the top section 30, an outer boot adapter panel 32A, B includes a panel 32A which is connected along a straight scored fold line 32C to an outer boot adapter panel 32B, which is connected along arcuate skip-scored fold line 30A to the rear end of top panel 30B. A portion of an elongated inhaler opening 114 bounded by scalloped sections 4B, which are formed by slits 4C, is aligned with a corresponding portion of half-opening 4B in inner boot adapter panel 2A.

Outer mouthpiece section 71 is connected along straight scored fold line 57 to top panel 30B. Circular openings 72 may be symmetrically formed in both top panel 30B and outer mouthpiece section 71, so as to be bisected by scored fold line 57. In another example, openings 72 may be any suitable shape, such as square, rectangle, oval, and the like. In another example, openings 72 may be located at any suitable point along top panel 30B. For instance, openings 72 may be exclusively located on top panel 30B or exclusively located on mouthpiece section 71. Or, openings 72 may be asymmetrically formed in both top panel 30B and mouthpiece section 71.

In one example, exhalation valve 126 (shown in FIG. 1A) may be formed on bottom section 2. A pair of exhalation valve openings 73 may be formed in bottom panel 2B, with an exhale membrane 75 attached along one side of exhalation valve openings 73 so as to cover them, and to flex away from exhalation valve openings 73 when a user exhales into inner volume 122 of inner housing 120. This allows exhaled breath to be exhausted through exhalation valve openings 73, and to seal them closed when the user inhales through openings 72.

Inner housing section 79 includes an elongated, trapezoidal panel 79A connected along straight scored fold line 41 to bottom panel 2B and a rectangular panel 79B connected along a straight scored fold line 63 to panel 79A. An elongated opening 12 in panel 79A becomes aligned with exhalation valve openings 73 when panel 79A is folded against the inner surface of bottom panel 2B as shown in FIG. 1A. When assembled, the portion of the apparatus 100 wherein opening 72A is located may be the mouth opening side of the apparatus 100. Outer mouthpiece section 71 also includes an opening 114 configured to overlie exhalation valve openings 73 when the apparatus is assembled and expanded for use.

In one example, an elongated rectangular opening 72A is symmetrically formed in bottom panel 2B and panel 79A so as to be bisected by fold line 41. Opening 72A may be any suitable shape to work in conjunction with openings 72. Opening 72A may comprise one or more openings to work in conjunction with openings 72. Opening 72A may be located at any point on bottom panel 2B or panel 79A to work in conjunction with openings 72. For instance, depending on the location of openings 72, opening 72A may be located entirely on bottom panel 2B, entirely on panel 79A, or asymmetrically formed within both bottom panel 2B and panel 79A.

Panel 79B is connected to another panel 79C along a straight scored fold line 87. A rectangular inhalation valve opening 93 is formed centrally in panel 79C. A rectangular inhalation membrane 76 is adhesively attached to the outer surface of the sheet 101 so as to cover inhalation valve opening 93 and flex to uncover inhalation valve opening 93 as the user inhales through openings 72 and 72A. Also, the opening of the flap necessarily causes a change in airflow direction, which has been shown to be advantageous in further reducing CPD in some papers. Panel 79E may be adhesively connected to the exterior of panel 2B upon assembly.

Panel 79C is attached to trapezoidal panel 79D along a straight skip-scored fold line 92. Preferably, inhalation valve opening 93 is as large as can be practically fit into panel 79C while nevertheless providing adequate room both for attachment of inhalation membrane 76 to panel 79C and for proper operation of inhalation membrane 76.

Trapezoidal panel 79E is connected to panel 79D along a continuously scored fold line 94. In one example, opening 95 is located symmetrically between panels 79D and 79E.

Side panels 96 and 97 are connected to panels 79B and 79C along straight, continuously-scored fold lines 98 and 99. Side panels 96 and 97, which are unique to the instant invention, and make the interface between the first volume 112 and the inner volume 122 substantially air tight, and which differentiate the instant apparatus from the LiteAire® device and apparatus disclosed in prior U.S. Pat. No. 6,679,252, are discussed in greater detail in FIG. 2, below.

It should be noted that all openings may have any size, shape, orientation, number, and placement suitable to work in conjunction with each other and to facilitate use by a user. FIGS. 1A and 1B show exemplary openings generally located centrally on the apparatus 100.

Figure 2:
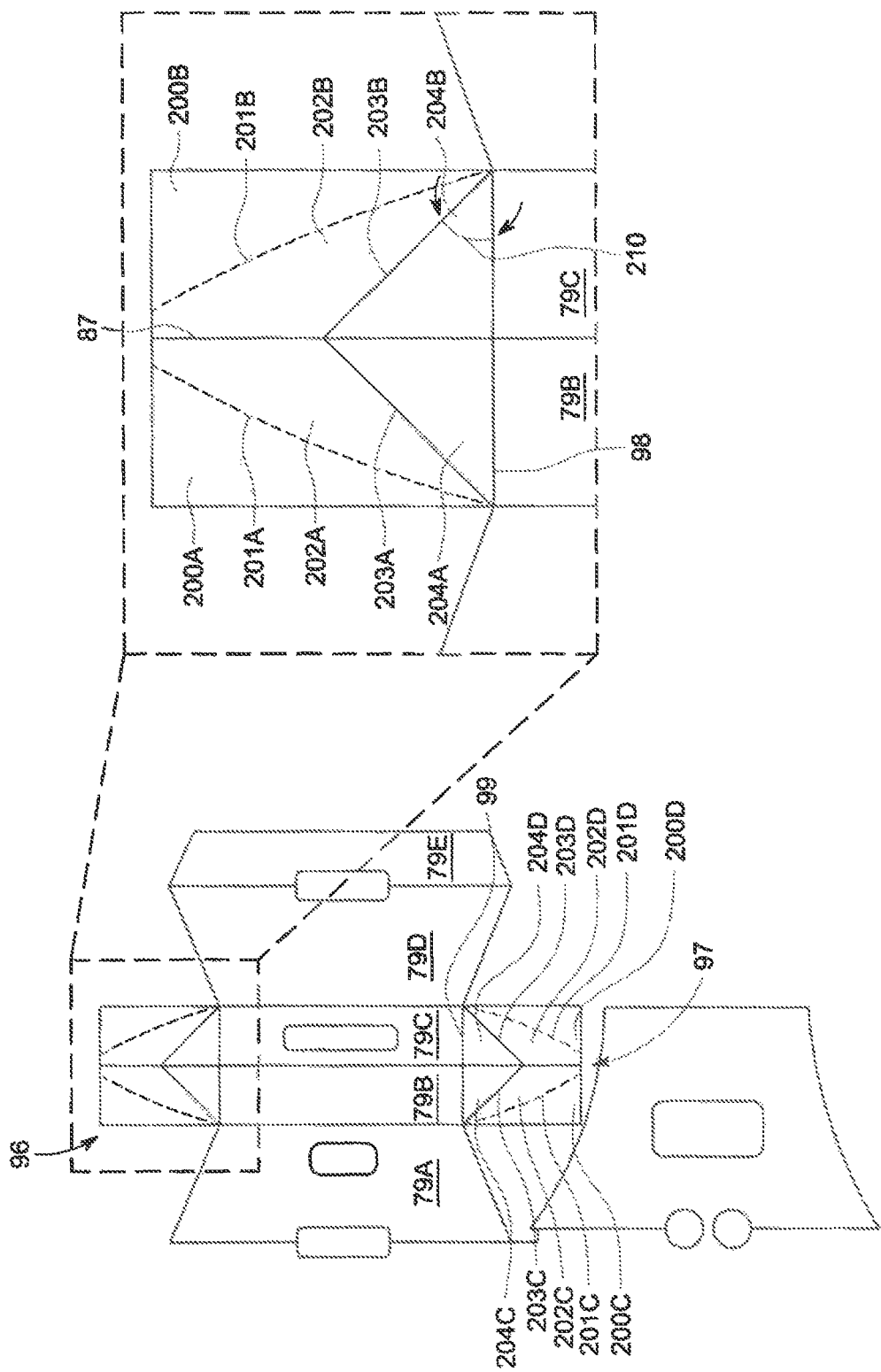
FIG. 2 is a close-up plan view of the sheet of FIG. 1B, in accordance with a first exemplary embodiment of the present disclosure.

FIG. 2 is a close-up plan view of the sheet 101 of FIG. 1B, in accordance with a first exemplary embodiment of the present disclosure. FIG. 2 shows the portion of the sheet 101 that, when assembled, forms the inner housing 120 of FIG. 1A. Panels 79A-E are shown connected by score lines. Connected to panels 79B and 79C are side panels 96 and 97. In the example shown in FIG. 2, side panels 96 and 97 are the same design on opposite sides of side panels 79B and 79C. Left and right sides of side panels 96 and 97 are also symmetrical about line 87.

Side panel 96 is shown within the close-up inset. Side panel 96 is shown as a rectangular panel comprising several flaps differentiated by diagonal scoring or perforation lines. On the left side, flaps 200A and 202A are differentiated by skip-scored fold line 201A. Flaps 202A and 204A are differentiated by perforation or scored line 203A. And flap 204A is differentiated from panel 79B by continuous score line 98. On the right side, flaps 200B and 202B are differentiated by skip-scored fold line 201B. Flaps 202B and 204B are differentiated by perforation line 203B. And flap 204B is differentiated from panel 79C by continuous score line 98. In one example, the angle 210 between score line 98 and perforation fines 204A or 204B may be 45°. The angle 210 may be mor or less depending on the size and shape of the flaps.

Side panel 97 comprises reciprocal flaps differentiated by diagonal scoring or perforation lines. On the left side, flaps 200C and 202C are differentiated by skip-scored fold line 201C. Flaps 202C and 204C are differentiated by perforation line 203C. And flap 204C is differentiated from panel 79B by continuous score line 99. On the right side, flaps 200D and 202D are differentiated by skip-scored fold line 201D. Flaps 202D and 204D are differentiated by perforation line 203D. And flap 204D is differentiated from panel 79C by continuous score line 99. In one example, the angle between score line 99 and perforation lines 204C or 204D may be 45°. The angle may be more or less depending on the size and shape of the flaps.

The left and right sides of side panels 96 and 97 are differentiated by continuous score line 87, which runs from side panel 96, between panels 79B and 79C, and through side panel 97. Each of the score or perforation lines 201A-D, 203A-D, 98, 99 runs from a point along line 87 to an outer corner of the side panel 96, 97.

When assembled, the side panels 96, 97 fold inward to create an inner housing 120. The side panels 96, 97 become sidewalls for the housing 120. While the chamber itself is not airtight, the interface between the inner volume and the outer volume is substantially airtight. Additionally, the sidewalls limit fluid connection with the first volume 112 and the ambient external environment of the apparatus 100.

Referring to FIGS. 1A-2, the apparatus 100 may be constructed from the sheet 101 as follows. For ease of description, reference will be made to the "topside" and "underside" of the panels and flaps comprising sheet 101, the "topside" being the portion of the panel or flap visible in FIGS. 1B, 2, while the "underside" is the opposite side not visible in the drawings.

In one example, the apparatus 100 is cut or punched from a single, unitary sheet 101 of suitable material, such as solid bleached sulfate paperboard, plastic, spun nonwoven polymer such as TYVEK® by DuPont, or the like. In another example, the apparatus 100 may be assembled from a plurality of pieces or sheets of suitable material. The material may be an antistatic or static dissipative paper to reduce static deposition of medicine particles on the walls of the apparatus 100. In one example, the sheet 101 may be coated in a static dissipative coating or the like. Inhalation valve 124, exhalation valve 126, and optional viewing window 8 may be first created by adhesively attaching membranes 76, 75, 8 to the appropriate surface of sheet 101 as discussed relative to FIG. 1B. The membranes 76, 75, and 8 may be any suitable material capable of creating a substantially airtight valve or window while also remaining flexible. In one example, the membranes 76, 75, and 8 may be a thin plastic, and polymer, and the like.

The inner housing 120 may be assembled next. The panels and flaps may be fixed or glued together using one or more suitable adhesives. The folding and gluing process starts by applying adhesive to the underside of panel 79A. Panel 79A is folded over so that the adhesive side contacts the underside of bottom panel 2B. Line 87 and the diagonal folds 201A-D, 203A-D run upward and toward the topside of panels 79B, 79C. Adhesive is applied to the underside of flaps 200A-D. Line 87 and lines 204A, B are used to fold panel 96 as a reverse fold to line up the undersides of panels 200A and 200B to the topsides of panels 79A and 79D, respectively. Line 87 and lines 204C, D are used to fold panel 97 as a reverse fold to line up the undersides of panels 200C and 200D to the topsides of panels 79A and 79D, respectively. Panels 79A and 79D are folded along lines 63 and 92, respectively, to bring the topsides of these panels into the corresponding undersides of panels 200A-D. Glue is applied to the topside of panel 79E. Panel 79E is folded along line 94 and glued to the topside of bottom panel 2B.

The outer housing 110 may be assembled around the inner housing 120 next. Adhesive is applied to the underside of panel 79D. The sheet 101 is folded along line 180C so that the undersides of top panel 2 and bottom panel 30 are folded toward one another. The underside of panel 79D is glued to the underside of top panel 30B. Glue is applied, in any appropriate order, to the undersides of panels 47A and 32A. Panel 47A is glued to the topside of panel 47. Panel 32A is glued to the topside of panel 2A. Glue is applied to the underside of panel 71, which is folded along line 57 and glued to the topside of bottom panel 2B over panel 79E.

Figure 3:
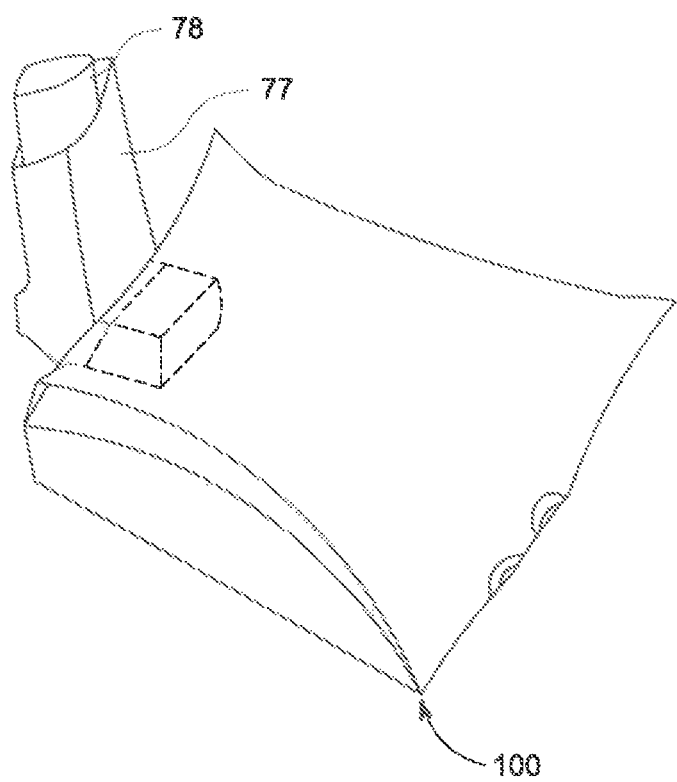
FIG. 3 is a perspective view of the apparatus in an expanded state, in accordance with a first exemplary embodiment of the present disclosure.

FIG. 3 is a perspective vie of the apparatus 100 in an expanded state, in accordance with a first exemplary embodiment of the present disclosure. In the expanded state, apparatus 100 is capable of receiving the mouthpiece end of the boot adapter 77 of a conventional inhaler containing an MDI canister 78 inserted through inhaler opening 114 shown in FIGS. 1A and 1B.

Referring to FIGS. 1A-3, the apparatus 100 may be expanded as follows. When the apparatus 100 is assembled as described above, it is in its flat or collapsed state. If the user presses right side panels 180A and 180B inward toward left side panels 47A and 47B so that they "unfold" along straight, scored fold lines 180C and 47C, respectively, the apparatus 100 pops up into and retains the configuration shown in FIG. 3. The fold lines 63, 87, and 92 allow panels 79B and 79C to be pulled by adhesive and 79D and the rising upper panel 30B upward from their generally horizontal position when apparatus 100 is collapsed so that the panel 79B,C is in a nearly vertical position when apparatus 100 is fully "popped up".

Figure 4:
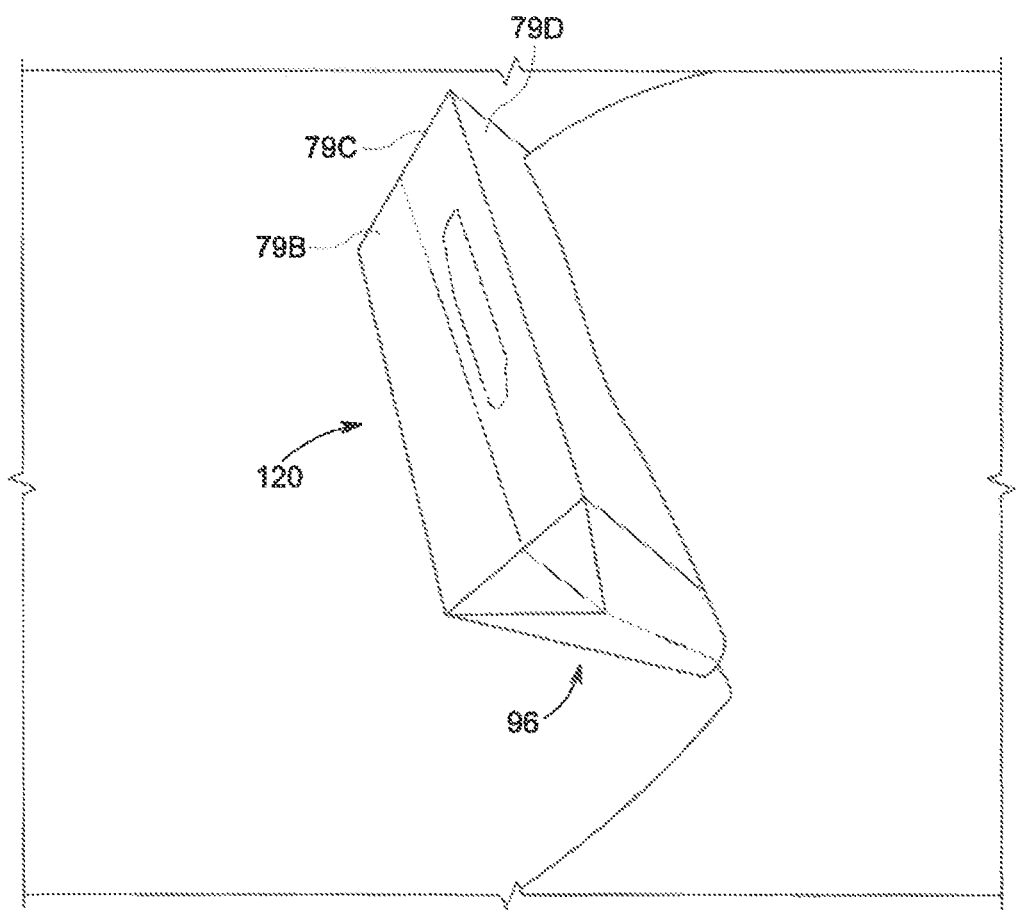
FIG. 4 is a perspective view of the inner housing in an expanded state, in accordance with a first exemplary embodiment of the present disclosure.

Additionally, when the boot adapter 77 with an MDI canister 78 therein is inserted into opening 114, that causes boot adapter panels 32A and 32B to unfold to the maximum extent FIG. 4 is a perspective view of the inner housing 120 in an expanded state, in accordance with a first exemplary embodiment of the present disclosure. In the exemplary embodiment shown in FIG. 4, inner housing 120 is a pyramid connected by panels 79D, 79C, 79B, 96, 97 (not shown), and 79A (not shown). Score line 201A is folded, where score line 203A is not folded, meaning panels 204A and 202A are coplanar, and panel 200A is roughly at a 90° angle with panels 204A and 202A. Panel 97, on the opposite side, has the same configuration. The expanded inner housing 120 may be shaped as any hollow polyhedron connected by panels. In one example, a number of the panels substantially abut portions of the outer housing 110. For instance, the inner housing 120 shown in FIG. 4 may abut the outer housing 110 at panels 96, 97, 79A, and 79D. An inner housing 120 with more sides may abut the outer housing on additional sides.

Referring to FIGS. 1A-4, the inner housing 120 may be expanded as follows. The outer housing 110 of the apparatus 100 is unfolded as described above. As this unfolding occurs, and as right side panels 180A and 180B move inward and engage side panel 97, side panel 97 also is pressed inward. Similarly, as left side panels 47A and 47B move inward and engage side panel 96, side panel 96 also is pressed inward. This causes side panels 96, 97 to fold along fold lines 98, 99 into the configuration shown in FIG. 4. Thus, side panels 96, 97 form a seal with panels 79A-D. Left side panels 47A-B and right side panels 180A-B reinforce the seal by supporting side panels 96 and 97. This effectively reduced or minimizes both inhaled air and exhaled air from bypassing the inhalation valve, substantially increasing the efficiency of the apparatus 100 by reducing or minimizing air inadvertently exhaled (rather than inhaled) by a user during activation of an MDI canister in a boot adapter from being forced around panels 79B and 79C. Additionally, this prevents the inadvertently exhaled air from forcing some of the MDI medication to leak out into the atmosphere between the periphery of opening 114 and the periphery of the MDI boot adapter. The efficiency of the apparatus 100 is thereby increased substantially.

Figure 5:
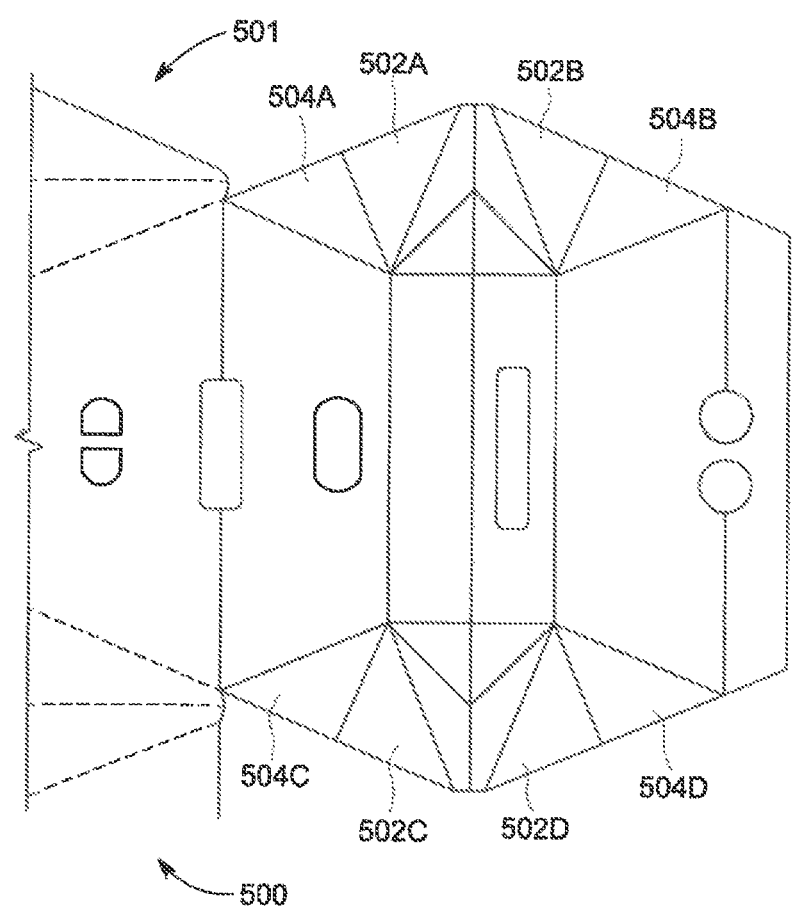
FIG. 5 is a close-up plan view of a sheet from which the apparatus is constructed, in accordance with a second exemplary embodiment of the present disclosure.

FIG. 5 is a close-up plan view of a sheet 501 from which the apparatus 500 is constructed, in accordance with a second exemplary embodiment of the present disclosure. In one example, the design of the sheet 501 may be substantially similar to sheet 101 shown in FIG. 1B, with the exception of additional flaps 502A-D, 504A-D used to form the sides of the inner housing. The additional flaps 502A-D, 504A-D are folded along the score lines shown to create webbed panels of the inner housing. These folded, webbed panels make the inner housing more airtight at the corners of the housing wall when expanded by providing a more robust seal. Other webbed panel designs may be used to provide an airtight seal at the corners of the inner housing.

FIG. 6 is a flowchart 600 describing a method of expanding a medication inhalation apparatus from an initially flat, collapsed state, in accordance with a first embodiment of the present disclosure. It should be noted that any process descriptions or blocks in flow charts should be understood as representing modules, segments, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

In step 610, an outer housing, an inner housing positioned within the outer housing, wherein the outer housing and the inner housing are substantially airtight when expanded, an inhaler opening formed at least partially within a sidewall of the outer housing at a first location, a mouth opening positioned within a sidewall of the outer housing and the inner housing at a second location, a one-way inhalation valve positioned within a sidewall of the inner housing, and a one-way exhalation valve positioned within a sidewall of the outer housing and the inner housing at a third location are provided in the collapsed state.

In step 620, a pair of opposite sidewall panels on the outer housing is pressed.

In step 630, the outer housing and inner housing are manually expanded to create a first volume encompassed by the outer housing and an inner volume encompassed by the inner housing, wherein the inhaler opening is in fluid communication with the first volume, wherein the mouth opening is in fluid communication with the inner volume, wherein the inhalation valve connects the first volume and the inner volume, wherein the exhalation valve connects the inner volume and the exterior of the outer housing, and wherein gas is flowable from the metered dose inhaler to the first volume, from the first volume to the inner volume, and from the inner volume to the mouth of a user.

Figure 7:
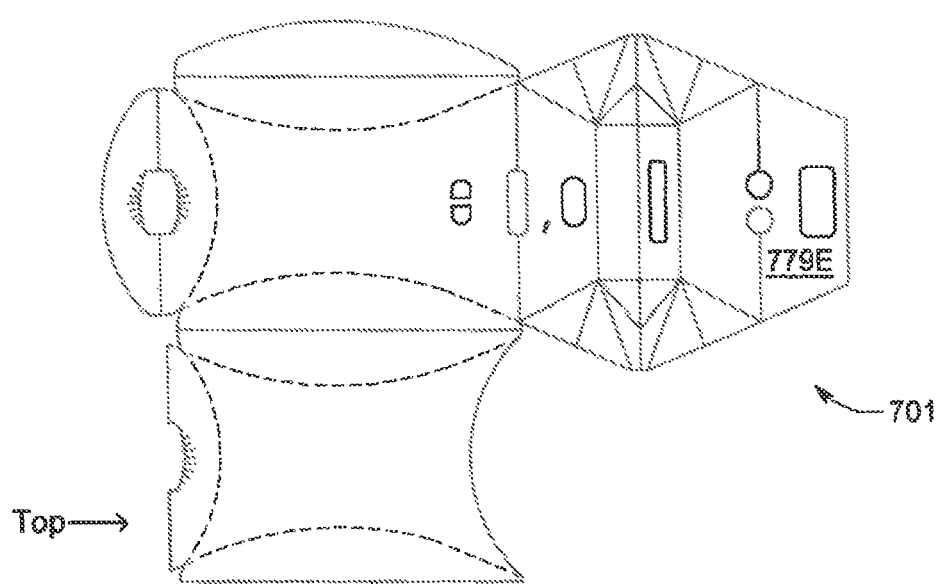
FIG. 7 is a plan view of a sheet from which the apparatus in accordance with a third embodiment of the present disclosure is constructed.

FIG. 7 is a plan view of a sheet 701 from which the apparatus is constructed, in accordance with a third exemplary embodiment of the present disclosure. In this example, the design of the sheet 701 is substantially similar to sheet 101 shown in FIG. 1B, with the additions shown in FIG. 5. However, in this ease the front panel 779E for the inner housing, corresponding to panel 79E of the FIG. 2 embodiment, is elongated. Front panel 79E is used to form the mouthpiece, instead of a panel 71 from the outer housing of FIG. 1B, folding to form the mouthpiece. Other than that, the FIG. 7 embodiment is similar to the FIG. 1B embodiment.

Operating Example

The following operating example may illustrate how the apparatus 100 is used in implementation.

The apparatus 100 may be assembled as described relative to FIGS. 1A-2 above. The outer housing 110 may be expanded as described relative to FIG. 3, and the inner housing 120 expanded as described relative to FIG. 4. A user may insert the mouthpiece end of the boot adapter 77 of an inhaler container an MDI canister 78 through the inhaler opening 114 of the apparatus 100 until it fits snugly. The user may place their mouth on the mouth opening 116, and may exhale into the inner housing 120. The user's exhaled breath may exit the inner housing 120 through the exhalation valve 126. Increased pressure in the inner housing 120 may cause membrane 75 to flex away from exhalation valve openings 73, allowing the exhaled breath to escape the apparatus 100. As the user finishes exhaling, the membrane 75 may return to its "closed" position on the apparatus 100, reducing or minimizing the amount of air entering the apparatus 100. The user may next engage the MDI canister 78 to spray medicine into the first volume 112 of the outer housing 110. The medicine may briefly remain in the first volume 112. The user may inhale through the apparatus 100, causing the inhalation valve 124 to open. Membrane 76 may flex into the inner volume 122 of the inner housing 120, allowing the medicine to travel from the first volume 112 to the inner volume 122. As the user continues to inhale, the medicine may continue to travel from the inner volume 122 into the user's mouth through the mouth opening 116. After the user has finished inhaling, the membrane 76 may return to its "closed" position on the inner housing 120, reducing or minimizing the amount of air from the outer housing 110 from entering the inner housing 120.

In some examples, the user may perform some of the steps in a different order. For instance, the user may engage the MDI canister 78 to spray before exhaling, or the user may wait some time between engaging the MDI canister 78 and inhaling. The apparatus 100 is designed to deliver an effective dose even under these conditions.

Test Examples

The following test example may illustrate the effectiveness of the apparatus 100 in creating a medication inhalation apparatus with improved medication delivery.

Three units of the subject apparatus 100, made from 16 pt SBS paperboard, were tested against a Monaghan Aerochamber Z-stat, a non-disposable valved holding chamber. The particle size distributions of the two devices were compared with both coordinated and uncoordinated breathing. Coordinated breathing is defined as actuation of the MDI occurring during the onset of user inhalation. Uncoordinated breathing is defined as actuation of the MDI occurring during the onset of user exhalation. A good metric of the efficacy of the apparatus 100 to mitigate user incoordination is the amount of dose lost from the coordinated breathing test to the uncoordinated breathing test. The Aerochamber unit tested gave a 38% drop in total emitted dose from coordinated to uncoordinated breathing, while the subject apparatus 100 showed, on average, no drop from coordinated to uncoordinated breathing in total emitted dose.

Thus, the invention provides a disposable "pop up", valved apparatus 100 which also allows for natural inhalation and exhalation by a user. The described valved apparatus 100 can be maintained in a collapsed, flat configuration, suitable for storage in a pocket, pocketbook or a briefcase, and expanded just prior to use, after which it can be discarded or re-folded for later use by the same user. The described apparatus 100 may be used by health care workers to demonstrate its use to users needing to receive an aerosol medication from an MDI inhaler. The apparatus 100 also is well suited for use in hospital emergency rooms, health-care clinics, pulmonary function labs, or infirmaries. In addition, its portability and low cost make it ideal for use by relief or world health organizations, especially when aerosol vaccines become available.

A medication inhalation apparatus 800 now will be discussed relative to FIGS. 8A-8C and 9. The apparatus 800 may be formed from a sheet 801. The sheet 801 may be cut, folded, scored, perforated, secured, and formed in a similar manner to the sheet 101 in FIGS. 1A-1B and as described herein below, depending on the shape and placement of lines and perforations in the sheet 801. In one example, the sheet 801 may be made from the same materials as the sheet 101 discussed above relative to FIGS. 1A-1B, and may be secured using the same adhesives and methods. For instance, the sheet 801 may be constructed from a single piece of stock. The single piece may be sheet stock. In another example, the sheet 801 may be at least partially constructed from antistatic material.

Figure 8A:
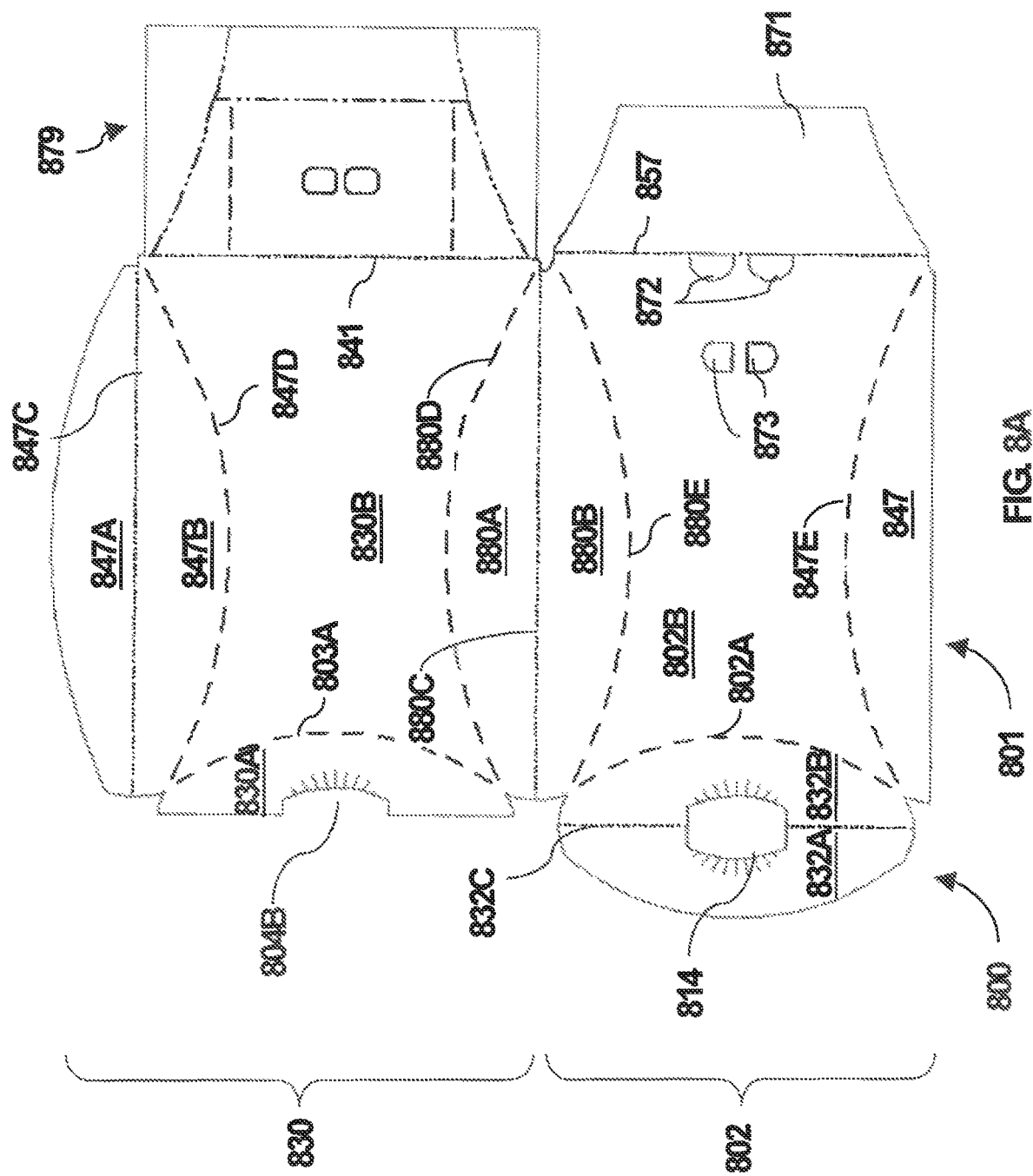
FIG. 8A is a plan view of a sheet from which a medication inhalation apparatus is constructed, in accordance with a fourth exemplary embodiment of the present disclosure.

FIG. 8A is a plan view of a sheet 801 from which the medication inhalation apparatus 800 is constructed, in accordance with a fourth exemplary embodiment of the present disclosure. The sheet 801, when assembled, pops up into the expanded state shown in FIG. 9. FIG. 8A shows the interior side of the sheet 801, i.e., the side that forms the interior of the apparatus 800 as assembled. Sheet 801 includes a bottom section 802, a top section 830, an inner flap 879, and an outer mouthpiece section 871. The inner flap 879 may form at least one boundary of a second volume within an outer housing formed by the sheet 801. The inner flap 879 is discussed in greater detail in FIG. 8B, and the second volume is discussed in greater detail in FIG. 9, below. Inner flap 879 is connected to top panel 830B along straight scored fold line 841. The bottom section 802 and top section 830 are connected by a right side section, which includes two right side panels 880A and 880B connected by a straight scored fold line 880C; as shown. Right side panel 880A is connected along an arcuate "skip-scored" or perfrated fold line 880D to top panel 830B, and right side panel 880B is connected along an arcuate skip-scored fold line 880E to bottom panel 802B.

On the bottom section 802, adhesive attachment panel 847 is connected by an arcuate scored or perforated fold line 847E to bottom panel 802B, and eventually is adhesively attached to the inner surface of left side panel 847A on top section 830. Left side panel 847A is connected to panel 847B across straight scored fold line 847C. Panel 847B is connected to top panel 830B by arcuate fold line 847D.

On the top section 830, the rear end portion of top panel 830B is connected along an arcuate skip-scored fold line 803A to an inner boot adapter panel 830A. Conversely, on the bottom section 802, an outer boot adapter panel 832A, B includes a panel 832A which is connected along a straight scored fold line 832C to an outer boot adapter panel 832B, which is connected along arcuate skip-scored fold line 802A to the rear end of bottom panel 802B. A portion of an elongated inhaler opening 814 bounded by scalloped sections formed by slits is aligned with a corresponding portion of half-opening 804B on top section 830A.

Outer mouthpiece section 871 is connected along straight scored fold line 857 to bottom panel 802B. Circular openings 872 may be formed in bottom panel 802B at the scored fold line 857. In another example, openings 872 may be any suitable shape, such as square, rectangle, oval, and the like. In another example, openings 872 may be located at any suitable point along bottom panel 802B. For instance, openings 872 may be exclusively located on bottom panel 802B or exclusively located on mouthpiece section 871. Or, openings 872 may be formed in both bottom panel 802B and mouthpiece section 871.

In one example, a pair of exhalation valve openings 873 may be formed in bottom panel 802B. The exhalation valve openings 873 may be covered by an exhale membrane such as the one described relative to FIGS. 1A-1B. This allows exhaled breath to be exhausted through exhalation valve openings 873, and to seal them closed when the user inhales through openings 872.

It should be noted that all openings may have any size, shape, orientation, number, and placement suitable to work in conjunction with each other and to facilitate use by a user. FIGS. 8A-8C and 9 show exemplary openings generally located centrally on the apparatus 800.

Figure 8B:
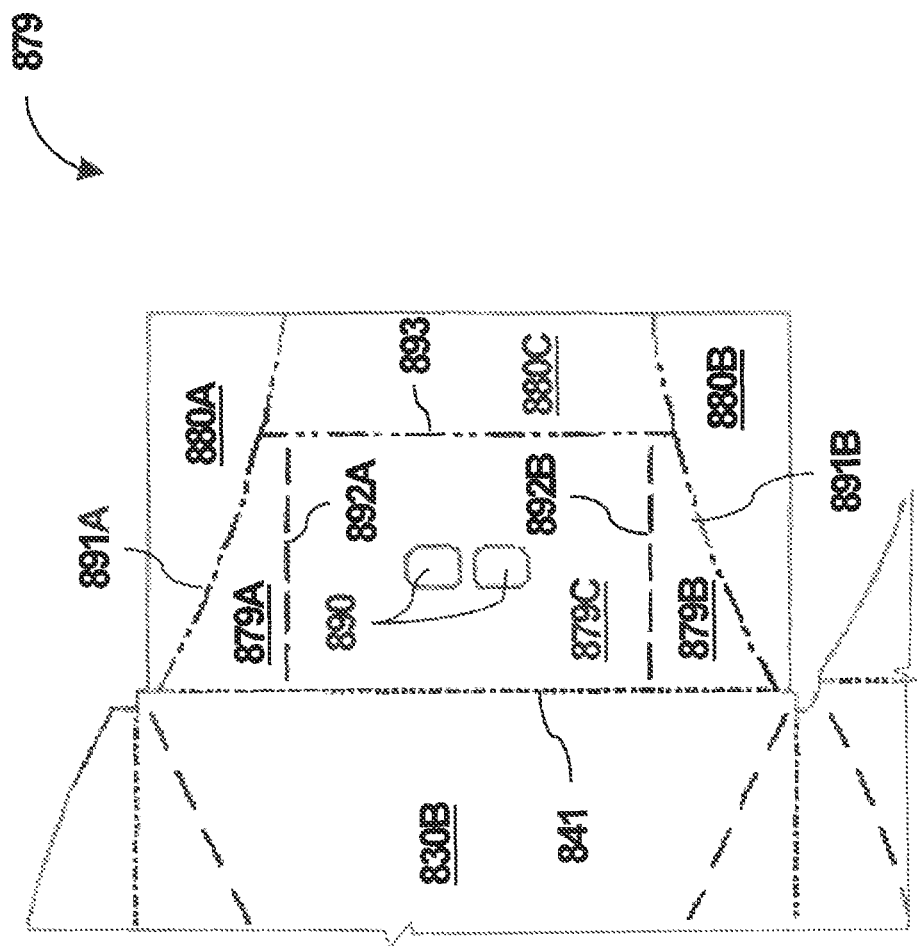
FIG. 8B is a close-up plan view of the inner flap shown in FIG. 8A, in accordance with the fourth exemplary embodiment of the present disclosure.

FIG. 8B is a close-up plan view of the inner flap 879 shown in FIG. 8A, in accordance with the fourth exemplary embodiment of the present disclosure. The inner flap 879 may be shaped as a rectangle comprising several panels joined across cut-score or skip-scored lines. Left outer panel 880A may be connected to left inner panel 879A and center outer panel 880C by a curved cut score 891A. Likewise, right outer panel 880B may be connected to right inner panel 879B and center outer panel 880C by a mirrored curved cut score 891B. Left and right inner panels 879A, B may be connected to center inner panel 879C across straight skip score lines 892A, 891B, respectively. Center inner panel 879C may be connected to center outer panel 880C across a straight cut score line 893. Valve openings 890 may be located at any suitable position on center inner panel 879C. There may be any number, size, shape, and orientation of valve openings 890 to allow gas to flow between the chambers of the apparatus 800. The inner flap 879 may be connected to top panel 830B along scored line 841. Scored line 841 may extend across the entirety of top panel 830B.

Referring to FIGS. 8A-8B, the apparatus 800 may be folded and assembled in the following manner: The inner flap 879 may be folded and glued as described herein to create a second volume within the apparatus 800 to allow a user to exhale air and inhale medicine. The inner flap 879 may be folded along scored line 841 onto the top panel 830B. An adhesive may be applied as described in FIG. 10, below. Inner flap 879 may be adhered to bottom panel 802B along the points of adhesive. Bottom panel 802B may be folded along straight scored fold line 880C to sandwich inner flap 879 between bottom panel 802B and top panel 830B. Outer boot adapter panel 832A may be folded along straight scored fold line 832C. Adhesive may be applied to outer boot adapter panel 832A, and outer boot adapter panel 832A may be glued to the underside of inner boot adapter panel 830A to secure the inhaler side of the apparatus 800. Adhesive may be applied to left side panel 847A. Left side panel 847A may be folded along straight scored fold line 847C over adhesive attachment panel 847. Left side panel 847A may be glued to the underside of adhesive attachment panel 847 to secure the side of the apparatus 800. Adhesive may be applied to outer mouthpiece section 871. Outer mouthpiece section 871 may be folded along scored fold line 857 to contact the underside of top panel 830. Outer mouthpiece section 871 may be glued to the underside of top panel 830 to secure the mouthpiece side of the apparatus 800.

Figure 8C:
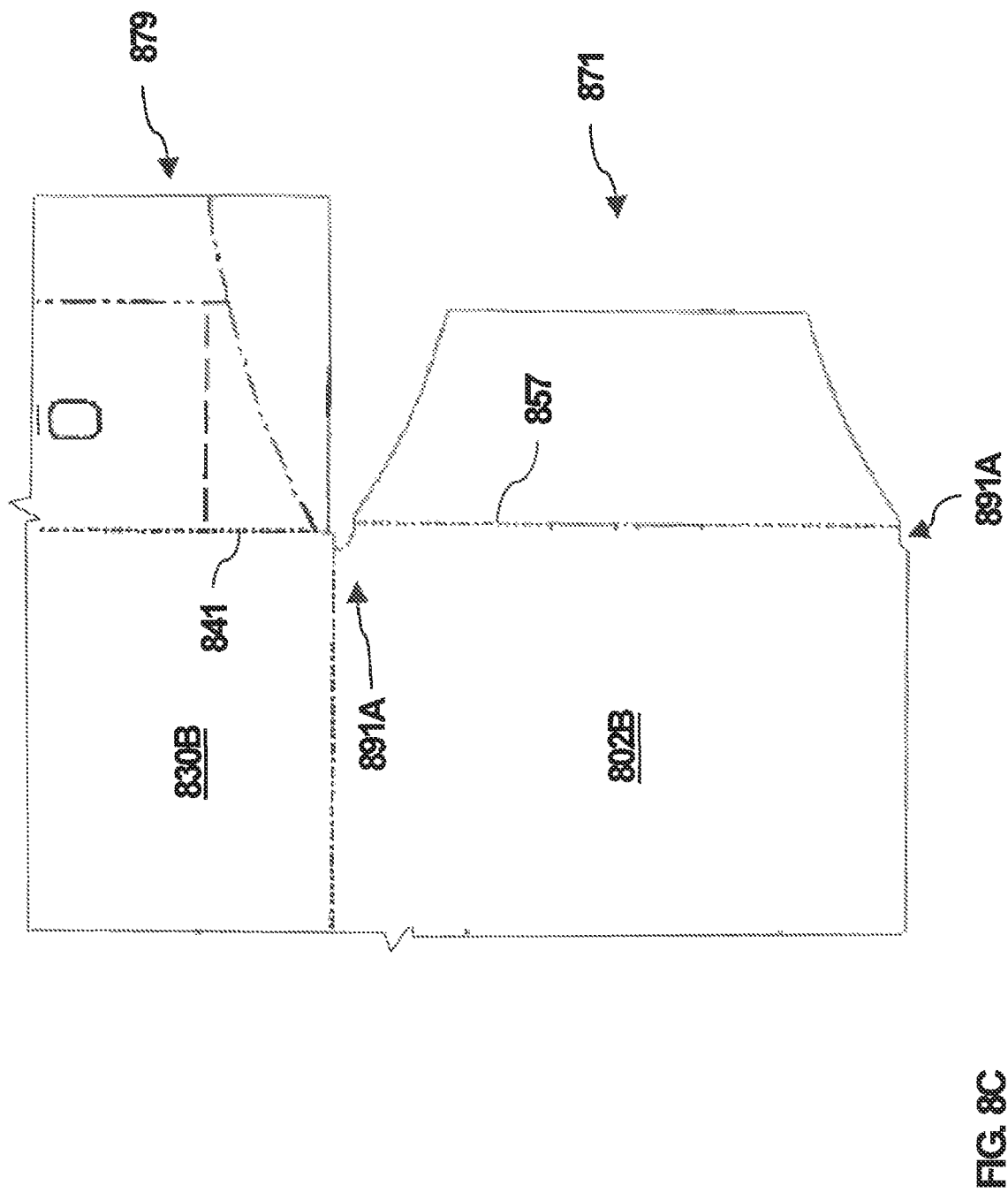
FIG. 8C is a close-up plan view of the outer mouthpiece section shown in FIG. 8A, in accordance with the fourth exemplary embodiment of the present disclosure.

FIG. 8C is a close-up plan view of the outer mouthpiece section 871 shown in FIG. 8A, in accordance with the fourth exemplary embodiment of the present disclosure. FIG. 8C shows the bottom panel 802B and the top panel 830B. The bottom panel 802B has receded corners 891A that are not squared—at a right angle—but are beveled inward toward the bottom panel 802B. When the apparatus 800 is folded, and the top panel 830B is located on top of the bottom panel 802B, the receded corners 891A allow the corners of the inner flap 879 to protrude past the corners 891A of the bottom panel 802B. This is important because when the apparatus 800 is folded and glued, there may be openings at the corners of the device. These receded corners 891A direct any air coming out of the corners out the sides of the apparatus 800 or toward the user, but not toward the first volume containing the drug. Directing the air in this way reduces the amount of air passing back into the first volume during user exhalation.

FIG. 8C also illustrates a difference in the alignment between scored line 841 and scored fold line 857. As shown in FIG. 8C, scored fold line 857 is located further to the right than scored line 841—meaning, in other words, that bottom panel 802B extends longer than top panel 830B. This may improve the shape of the inner flap 879 with respect to the second volume created when the apparatus 800 is expanded. When the apparatus 800 is expanded, the inner flap 879 is shorter than the length of the same point on the bottom panel 802B. Because of this, the inner flap 879 forms a straight line between the attachment surfaces—top and bottom panels 830B, 802B—while the bottom panel 802B matches the curved profile of perforated fold lines 880E, 847E. This creates a space between the inner panel 879 and the bottom panel 802B which may become the second volume and may be used as a mouthpiece for the apparatus 800.

There are many aspects of the design that contribute to the functioning of the apparatus 800. These design features are the receded corners on the outer flap 871, discussed above, the tension relief lines on the inner flap 879, and the perforation lines 847D, 880D near the mouthpiece. The design of the apparatus 800 means that a lot of tension exists in the inner flap 879 of the apparatus 800, namely in bending the inner flap 879 to form high points where the inner flap 879 attaches to the sides of the apparatus 800, and a low point in the middle of the inner flap 879. This type of "U" bend would be seen in the inhalation valve, which would increase the valve resistance, possibly out of specification, or cause creasing to occur around the vents 890 because they created a relief point for the tension. Both of these problems are overcome by the addition of the tension relief lines 892A, 892B. These tension relief lines 892A, B redirect the flexural tension to crease along these lines instead of across the inhalation vents. These lines may be perforated, though perforation would let a slight amount of air through the perforation cuts. A better option may be to use cut score lines instead of perforation lines. These lines may be straight, as depicted, or may also have any suitable shape or curvature.

The perforation lines 847D, 880D near the mouthpiece of the apparatus 800 are positioned so that the projected line made by the perforations meets the corners of the top panel 830B. This allows there to be little to no gap at the corner where the perforations 847D, 880D meet the corners of the top panel when the apparatus 800 is expanded. On the bottom panel, the perforations do not meet the corners, and so there is a slight opening at the corners when the apparatus 800 is expanded.

Figure 9:
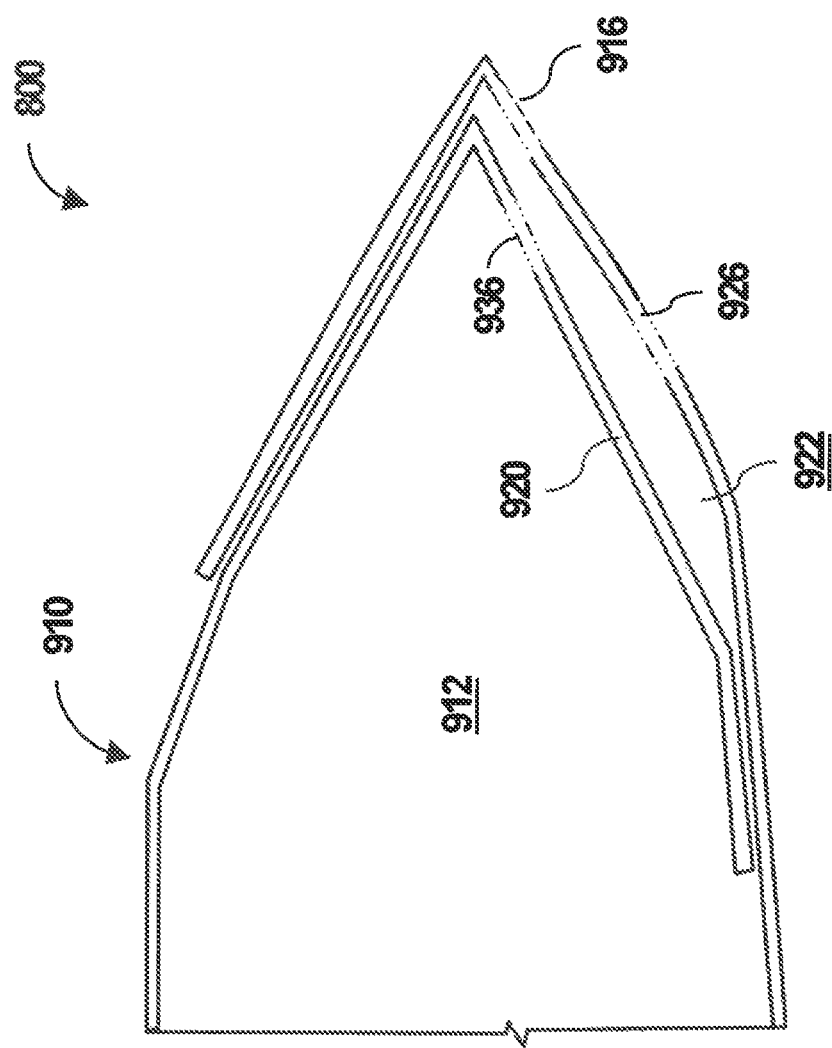
FIG. 9 is a longitudinal cross-sectional view of the medication inhalation apparatus in an expanded state, in accordance with the fourth exemplary embodiment of the present disclosure.

FIG. 9 is a longitudinal cross-sectional view of the medication inhalation apparatus 800 in an expanded state, in accordance with the fourth exemplary embodiment of the present disclosure. The expanded apparatus 800 may be discussed relative to FIGS. 1A-1B and 8A-8C. For ease of illustration, FIG. 9 shows only a portion of the expanded apparatus 800; the portion not shown, which includes the outer boot adapter panel 832A, B and inner boot adapter panel 830A, may be understood with reference to the analogous elements of FIGS. 1A-1B. It should also be understood that FIG. 9 shows folded portions of the apparatus 800 separated by a small distance. This is shown for ease of illustration only; in construction, layers of the sheet 801 folded together will be in contact with one another by adhesive or by biased force.

The apparatus 800 includes an outer housing 910 collapsible into a substantially flat configuration and expandable to bound a first volume 912 adapted to receive a plume of medication particles ejected by an MDI inhaler. An inner flap 920 is located within the outer housing 910 and, together with the outer housing 910, is expandable to bound a second volume 922 within the outer housing. A first opening, elongated inhaler opening 814 shown in FIG. 8A, is formed through a wall of the outer housing 910 at a first location in fluid communication with the first volume 912. The first opening 814 is adapted to accommodate a mouthpiece of an MDI inhaler (not shown). A second opening 916 is formed through a wall of the outer housing 910 at a second location adapted to form a user mouth opening in fluid communication with the second volume 922. A one-way inhalation valve 936 is located within the inner flap 920. The inhalation valve 936 connects the first volume 912 and the second volume 922. A one-way exhalation valve 926 is located within a wall of the outer housing 910. The exhalation valve 926 connects the second volume 922 and the exterior of the outer housing 910. In an expanded state, gas is flowable from a connected MDI to the first volume 912, from the first volume 912 to the second volume 922, and from the second volume 922 to the mouth of a user.

The outer housing 910 may be formed as described above using the top and bottom sections 830, 802. In a collapsed state, the outer housing 910 may be substantially flat, having the thickness of a few layers of the sheet 801. In an expanded state, the outer housing 910 may bound a first volume 912. The first volume 912 may be defined by the interior of the outer housing 910 and the inner flap 920. In use, the first volume 912 may be a chamber for holding medication particles sprayed from a connected MDI. The gas in the first volume 912 may remain in the first volume 912 until the user inhales the gas.

The inner flap 920 is located within the outer housing 910. The inner flap 920 extends between the top and bottom panels 830B, 802B and between side panels 847A, B and 880A, B. When the apparatus 800 is expanded, the inner flap 920 rises from a flattened configuration to a partially raised configuration, as shown in FIG. 9. When the inner flap 920 is partially raised, it creates a second volume 922 within the outer housing 910 bounded by the interior of the outer housing 910 and the inner flap 920. The second volume 922 is an intermediate volume between the first volume 912 and a user's mouth, and the user may inhale or exhale through the second volume 922 in order to receive the medication particles located in the first volume 912 or to clear the user's lungs of air before receiving the medication particles.

The first opening, which is shown in FIG. 8A as elongated inhaler opening 814, is expandable to receive an MDI inhaler. This is discussed in greater detail relative to FIG. 1A.

The second opening 916 is formed on the outer housing 910. A user may place their mouth over the second opening 916 and may inhale or exhale through the second opening 916. As discussed above, the second opening 916 may include one or more openings, such as circular openings 872, and may generally be located in close proximity to scored fold line 857. The second opening 916 may be any size, shape, or configuration of openings suitable to allow the user to inhale and exhale at sufficient flow rates through the apparatus 800. The second opening 916 is in fluid communication with the second volume 922 to allow gas to flow from the second volume 922 to the user's mouth or from the user's mouth to the exterior of the apparatus 800.

The one-way inhalation valve 936 is located on the inner flap 920. As shown in FIG. 8B, the inhalation valve 936 may include one or more openings 890 of any suitable shape, size, and configuration to allow gas to travel from the first volume 912 to the second volume 922. As described relative to FIG. 1B above, the inhalation valve 936 may include a flexible membrane (not shown) lying flat against the inner flap 920 over the one or more openings 890. The flexible membrane may flex away from the first volume 912 when a user inhales in order to allow gas from the first volume 912 to flow from the first volume 912 to the second volume 922. When the user exhales, the flexible membrane may remain flat against the inner flap 920 to cover the one or more openings 890.

The one-way exhalation valve 926 may be located on the outer housing 910 and may operate under the same principle as the inhalation valve 936. The bottom panel 802B may have one or more exhalation valve openings 873, which may be any suitable size, shape, and configuration to allow air to pass out of the apparatus 800. The exhalation valve 926 may include a flexible membrane (not shown) lying flat against the exterior side of the bottom panel 802B. The flexible membrane may flex away from the apparatus 800 when a user exhales, allowing air from the user's lungs and mouth to escape out of the apparatus. When the user inhales, the flexible membrane may remain flat against the bottom panel 802B, preventing exterior air from entering the second volume 922.

It should be noted that the one-way inhalation and exhalation valves 936, 926 may be made from any suitable materials, including plastic, paper, wood, polymer, and the like.

In use, a user may expand the apparatus 800 from its flattened state by pressing the sides of the apparatus 800, causing the top panel 830B to rise and the apparatus 800 to expand. The user may attach an MDI device to the apparatus 800. The user may press on the MDI device to release the medicine into the first volume 912. The user may place their mouth of the second opening 916 and may exhale through the second opening 916, into the second volume 922, and out the exhalation valve 926. The user may inhale, causing the medicine to travel from the first volume 912 to the second volume 922 through the inhalation valve 936, then into the user's mouth through the second opening 916.

The design relies on the tension created by mismatched geometry. When the apparatus 800 is flattened, the perforation lines 880E, 847E of the bottom panel 802B and the cut score splines 891A, B on the inner flap 879 line up, and the apparatus 800 is flat. When the apparatus 800 is expanded, the sides of the inner flap 879 stay glued to the sides of the bottom panel 802B and remain at the same height as the sides. Additionally, this causes the first volume 912 to be substantially larger than previously known designs, which may improve the holding capabilities of the first volume 912.

FIG. 10 is a close-up plan view of a glue pattern of the inner flap 879 shown in FIG. 8B, in accordance with the fourth exemplary embodiment of the present disclosure. Glue or other adhesive may be applied to the inner flap 879 or to the equivalent location on the bottom panel 802B in an "H" pattern before the inner flap 879 is folded over. The glue "H" pattern shown in FIG. 10 is an exemplary pattern showing the minimum locations where glue or adhesive may be applied in order to create a proper seal between the first volume, the second volume, and the outer housing. More glue lines may be applied as long as the pattern shown herein is also followed. Additionally, depending on the manufacture, the glue "H" pattern shown herein may be applied as a series of lines, broken lines, dots, and the like, as long as the glue or adhesive is applied to substantially seal along the entire adhesive lines.

The sheet 801 may be printed and die cut. Valve holes may be cut, and the valves may be assembled as discussed above. Lines 1080A, 1080B, and 1093 may be located on the underside of the inner flap 879. They are shown with reference to the topside of inner flap 879 for ease of illustration. However, it should be understood that the adhesive or glue may be applied as an "H" pattern so as to adhere the underside of the inner flap 879 to the bottom panel 802B of the apparatus 800. The glue or adhesive may be applied along lines 1080A, 1080B, and 1093, or along the equivalent locations on bottom panel 802B. Either before or after application, the inner flap 879 may be folded over onto the top panel 830B. The bottom panel 802B may be folded onto the inner flap 879 such that the inner flap 879 is sandwiched between the top and bottom panels 830B, 802B. The rest of the apparatus 800 may be folded as described above.

Operational Examples

The usefulness of the design is readily apparent from the backflow readings taken on the apparatus 800. The apparatus 800 delivered roughly 0.15 L/min of backflow without pinching the sides of the apparatus 800, which is a significant improvement over prior devices. Backflow is a decent predictor of the ability of the apparatus 800 to mitigate a user's inability to inhale at the same time as pMDI actuation, which is one of the major functions of a VHC. This improvement also runs hand in hand with decreased complexity in manufacturing compared with the apparatus 100 shown in FIGS. 1A-1B and 2. The folding process may use mountain and valley folds, which are routinely performed on folder/gluers. The ability to entirely perform the folding and gluing of the apparatus 800 on a folder/gluer means that the cost of manufacture can be lowered and the speed of production can be increased.

FIG. 11 is a close-up plan view of an inner flap 1179 for use in conjunction with the sheet 801 shown in FIG. 8A, in accordance with a fifth exemplary embodiment of the present disclosure. The inner flap 1179 may increase the size of the second volume 922 in FIG. 9 relative to the inner flap 879 shown in FIG. 8A. The inner flap 1179 may include left outer panel 1180A connected to left inner panel 1179A across skip scored fold lines 1181A and 1182A. Likewise, right outer panel 1180B may be connected to left inner panel 1179B across skip scored fold lines 1181B and 1182B. Center outer panel 1180C is connected to center middle panel 1179C across skip scored fold line 1193. Center middle panel 1179C may include one or more valve openings 1103 located on the center middle panel 1179C. Center middle panel 1179C may he connected to center inner panel 1100 across straight skip scored line 1102C and curved skip score lines 1102A and 1102B. Center inner panel 1100 may be connected to top panel 830B across fold line 841 and may extend substantially across a width of the inner flap 1179.

The inner flap 1179 shown in FIG. 11 may improve airflow through the apparatus 800 in cases where a user is likely to bite down on the apparatus 800 in use. In the embodiment shown in FIGS. 8A-9, the inner flap 879 is located in close proximity to the outer housing 910 in the expanded state. In the embodiment shown in FIG. 11, the inner flap 1179 may be glued to the top panel 830B at the center inner panel 1100. The center inner panel 1100 may act as an adhesive panel, securing a portion of the inner flap 1179 to the top panel 830B. This may cause the inner flap 1179 to be oriented more vertically in an expanded state than the inner flap 879 in FIGS. 8A-9, which in turn may create more space in the second volume 922.

Figure 12A:
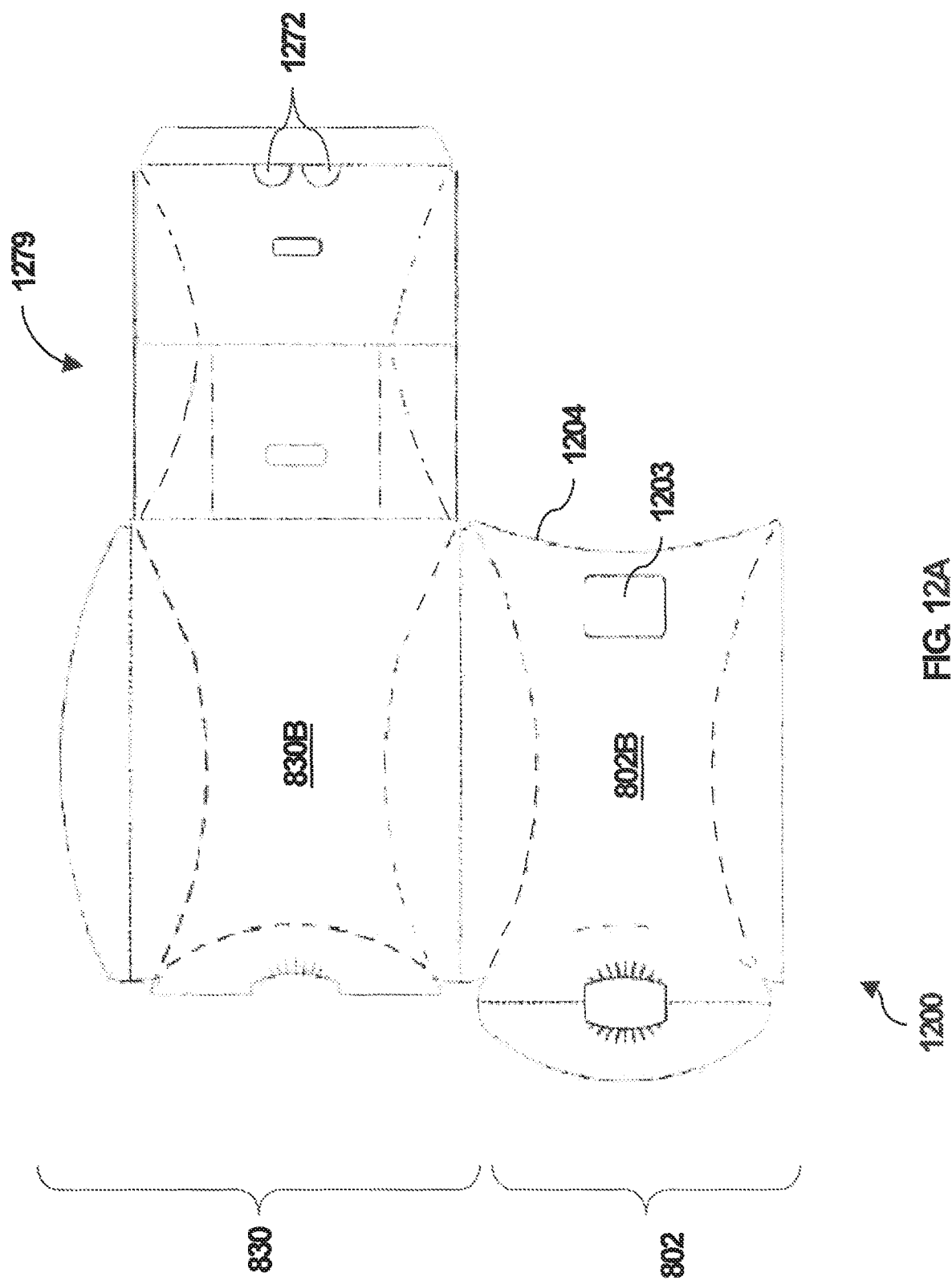
FIG. 12A is a plan view of a sheet from which a medication inhalation apparatus is constructed, in accordance with a sixth exemplary embodiment of the present disclosure.

FIG. 12A is a plan view of a sheet 1200 from which a medication inhalation apparatus is constructed, in accordance with a sixth exemplary embodiment of the present disclosure. In one example, the sheet 1200 may be include substantially the same component panels and fold lines as the sheet 801 shown in FIG. 8A, above. This may include top and bottom sections 830, 802 having top and buttom panels 830B, 802B, respectively. For ease of illustration, not all of the component panels and fold lines are given reference characters in FIG 2A. It should be understood that except as described below, the components of the sheet 1200 are substantially the same as sheet 801 above.

Sheet 1200 may include an inner flap 1279 for creating a separate, sealed mouthpiece chamber. This is discussed in greater detail in FIG. 12B, below.

In one example, sheet 1200 may not include an outer flap, such as outer flap 871 shown in FIG. 8A. In this example, bottom panel 802B may be folded over inner flap 1279 and adhered directly to inner flap 1279. Bottom panel 802B may be arcuate along edge 1204 so as not to cover circular openings 1272 on the inner flap 1279, which allow the user to exhale into and inhale out of the apparatus 1201 in an expanded state. Bottom panel 802B may also include one or more valve openings 1203 that covers the adhesive panel of the valve, while still allowing the free edge to open freely. Any suitable shape, number and size of valve openings 1203 may be used.

Figure 12B:
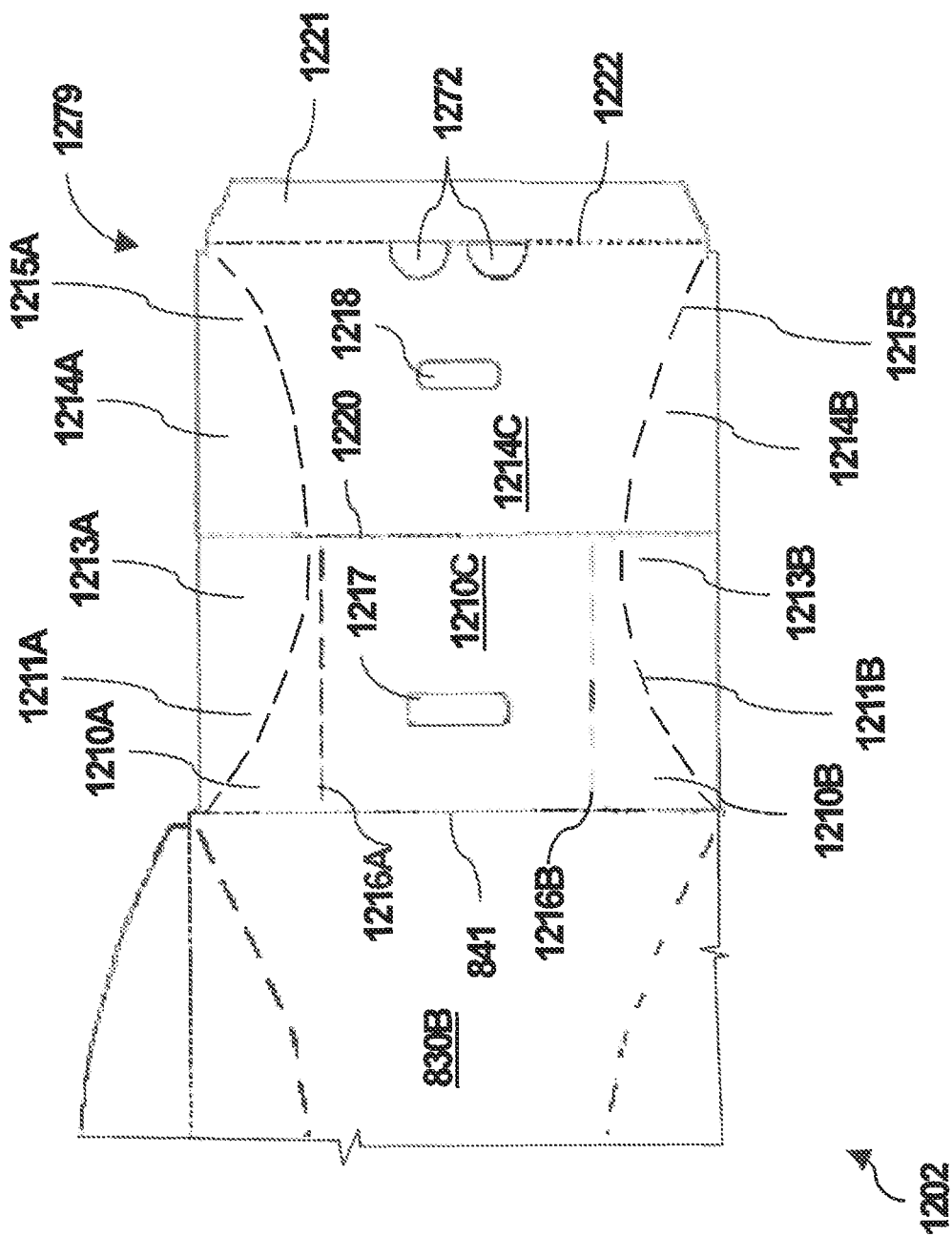
FIG. 12B is a close-up plan view of an inner flap for creating a separate mouthpiece chamber, in accordance with the sixth exemplary embodiment of the present disclosure.

FIG. 12B is a close-up plan view of an inner flap 1279 for creating a separate mouthpiece chamber 1202, in accordance with the sixth exemplary embodiment of the present disclosure. The mouthpiece chamber 1202, which may create a second volume when assembled and in an expanded state, may be a sealed chamber around which the rest of the apparatus 1201 is folded. This may improve the seal between the first volume and the second volume within the apparatus 800.

The inner flap 1279 may include left central panels 1210A and 1213A connected across cut scored line 1211A. Left central panel 1210A may be connected to central panel 1210C across skip scored fold line 1216A. Likewise, right central panels 1210B and 1213B may be connected across cut scored line 1211B. Right central panel 1210B may be connected to central panel 1210C across skip scored fold line 1216B. Central panel 1210C may include one or more valve openings 1217 located on the central panel 1210C. Left, right, and central panels 1210A, 1210B, 1210C may be connected to top panel 830B across fold line 841.

The central panels above may be connected to outer panels 1214A, 1214B, 1214C across fold line 1220, which may extend across the width of the inner flap 1279. Left outer panel 1214A and right outer panel 1214B may be connected to central panel 1214C across arcuate cut scored fold lines 1215A, 1215B, respectively. Central panel 1214C may include one or more valve openings 1218 located to align with valve opening 1203 when the apparatus 1201 is in an expanded state. Valve opening(s) 1218 may allow air to travel from the second volume, i.e., the mouthpiece chamber 1202, to the exterior of the apparatus 1201. Central panel 1214C may also include one or more circular openings 1272 to allow a user to breathe into or breathe from the apparatus 1201. The circular openings 1272 may allow air to flow between the second volume and the user's mouth.

Central panel 1214C may be connected to edge panel 1221 across fold line 1222, which may extend across the entire width of the inner flap 1279.

The apparatus 1201 may be assembled by folding the inner flap 1279 along line 841 on top of the top panel 830B. The outer panels may be folded back along line 1220, and the edge panel 1221 may be folded back along line 1222 to rest on the underside of the top panel 830B. Adhesive may be applied to the edge panel 1221 and to panels 1213A, 1213B, 1214A, 1214B. Bottom panel 802B may be folded over against top panel 830B, and the left side panel and adhesive side panel may be glued and attached as described above. The top of bottom panel 802B may be glued to the outer panels near the circular openings 1272. The boot adapter panels may be glued and attached as described above as well.

When in an expanded state, the apparatus 1201 may include an outer housing formed by the top and bottom sections 830, 802. The outer housing may be collapsible into a substantially flat configuration and expandable to bound a first volume adapted to receive a plume of medication particles ejected by an MDI inhaler. The inner flap 1279 may be located within the outer housing and may be expandable to bound a second volume within the outer housing. An edge panel 1221 of the inner flap 1279 may be adhesively affixed to a portion of the outer housing to secure the second volume. A first opening may be formed through a wall of the outer housing at a first location. The first opening may be in fluid communication with the first volume, and may be adapted to accommodate a mouthpiece of an MDI inhaler. A second opening may be formed through a wall of the outer housing at a second location and may be adapted to form a user mouth opening in fluid communication with the second volume. A one-way inhalation valve may be located within a central panel of the inner flap and may connect the first volume and the second volume. A one-way exhalation valve may be located within an outer panel of the inner flap and a wall of the outer housing. The one-way exhalation valve may connect the second volume and an exterior of the outer housing. In an expanded state, gas is flowable from a connected MDI to the first volume, from the first volume to the second volume, and from the second volume to the mouth of a user.

The separate mouthpiece chamber 1202 may improve over the art in at least two ways. In a first way, the apparatus 1201 may increase protection for the exhalation valve by providing a protective layer around valve opening 1203. The protective layer, which may essentially be the portion of the bottom panel 802B located around the valve opening 1203, may allow the exhalation valve to be recessed into the apparatus 1201. This extra layer allows the glue line of the exhalation valve to be covered and protected, and it also gives the free edge of the exhalation valve increased protection from being accidentally snagged when the apparatus 1201 is slid against other surfaces. In a second way, the application of adhesive is simplified compared to what is known in the art. Since the back of the mouthpiece is formed by a score line 1220, which blocks airflow, the only glue lines required to seal the mouthpiece chamber 1202 are the two glue lines on the side of the mouthpiece chamber 1202. This simplifies the glue pattern immensely since the gluing to form a sealed mouthpiece is no longer dependent on gluing with perpendicular glue lines, which can be difficult to perform on a folder/gluer.

Figure 13:
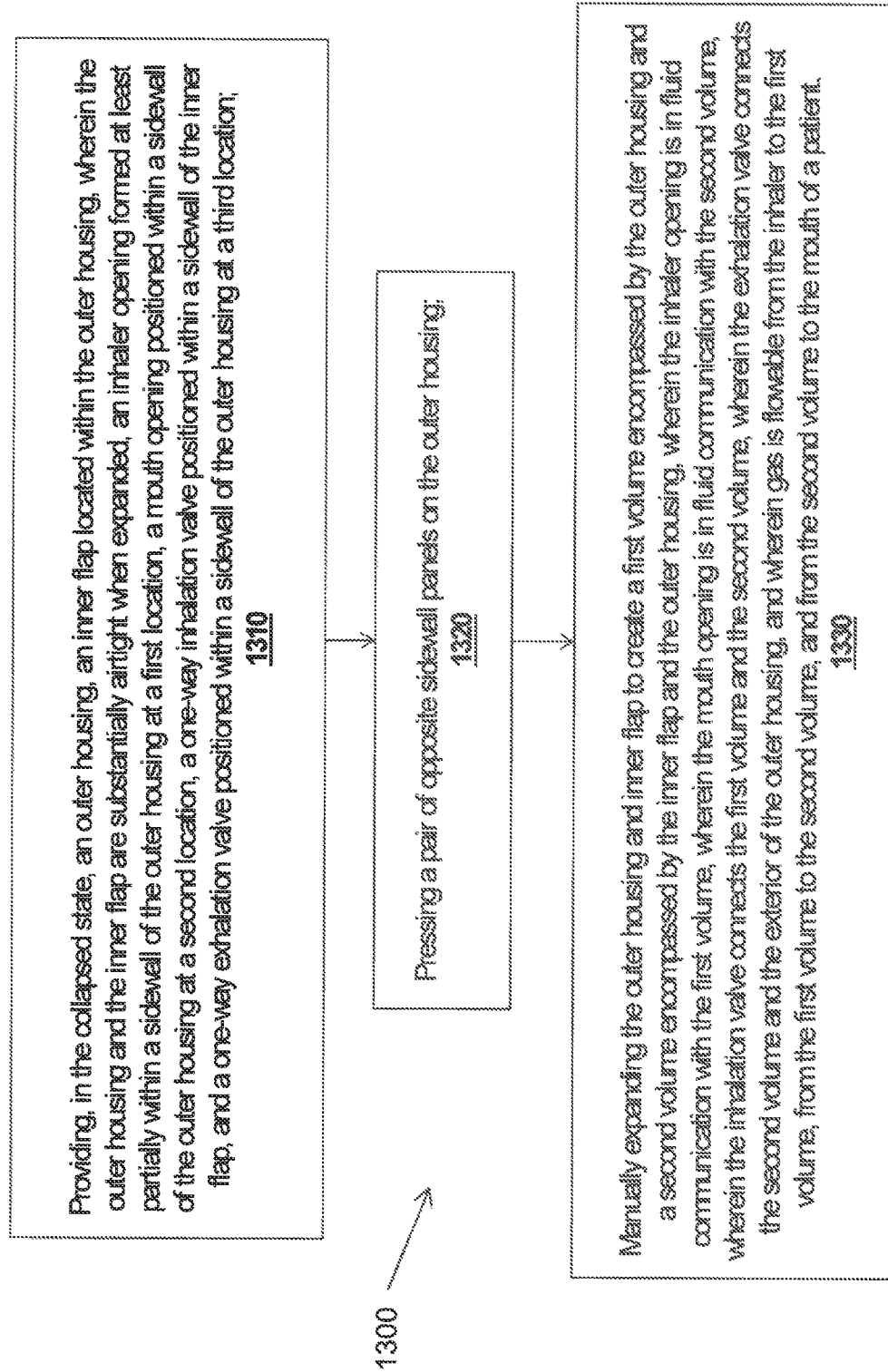
FIG. 13 is a flowchart describing a method of expanding a medication inhalation apparatus from an initially flat, collapsed state, in accordance with a first embodiment of the present disclosure.

FIG. 13 is a flowchart 1300 describing a method of expanding a medication inhalation apparatus from an initially flat, collapsed state, in accordance with a first embodiment of the present disclosure. It should be noted that any process descriptions or blocks in flow charts should be understood as representing modules, segments, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

In step 1310, an outer housing, an inner flap positioned within the outer housing, wherein the outer housing and the inner flap are substantially airtight when expanded, an inhaler opening formed at least partially within a sidewall of the outer housing at a first location, a mouth opening positioned within a sidewall of the outer housing at a second location, a one-way inhalation valve positioned within a sidewall of the inner flap, and a one-way exhalation valve positioned within a sidewall of the outer housing at a third location are provided in the collapsed state.

In step 1320, a pair of opposite sidewall panels on the outer housing is pressed.

In step 1330, the outer housing and inner flap are manually expanded to create a first volume encompassed by the outer housing and an second volume encompassed by the inner flap and the outer housing, wherein the inhaler opening is in fluid communication with the first volume, wherein the mouth opening is in fluid communication with the second volume, wherein the inhalation valve connects the first volume and the second volume, wherein the exhalation valve connects the second volume and the exterior of the outer housing, and wherein gas is flowable from the metered dose inhaler to the first volume, from the first volume to the second volume, and from the second volume to the mouth of a user.

While the invention has been described with reference to several particular embodiments thereof, those skilled in the art will be able to make the various modifications to the described embodiments of the invention without departing from the true spirit and scope of the invention. It should be emphasized that the above-described embodiments of the present disclosure, particularly, any "preferred" embodiments, are merely possible examples of implementations, merely set forth for a clear understanding of the principles of the disclosure. It is intended that all elements or steps which are insubstantially different or perform substantially the same function in substantially the same way to achieve the same result as what is claimed are within the scope of the invention. For example, an exhalation valve or other port may be provided on any portion of the inner housing/outer housing. Various other ways of folding the sheet material to achieve the collapsed/expanded configurations can be provided. Different arrangements of lock tabs and lock tab receiving slots than disclosed herein could be provided, or Velcro or similar attachment materials could be used. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. A medication inhalation apparatus, comprising:
    an outer housing, collapsible into a substantially flat configuration and expandable to bound a first volume adapted to receive a plume of medication particles ejected by an MDI (metered dose inhaler);
    an inner flap located within the outer housing and, together with the outer housing, expandable to bound a second volume within the outer housing, wherein the inner flap includes first, second, third, fourth and fifth panels connected to one another along straight scored fold lines;
    a pair of side panels connected to the second and third panels along further straight scored fold lines;
    a first opening formed through a wall of the outer housing at a first location, in fluid communication with the first volume, and adapted to accommodate a mouthpiece of the MDI;
    a second opening formed through a wail of the outer housing at a second location adapted to form a user mouth opening in fluid communication with the second volume;
    a one-way inhalation valve located within the inner flap, the inhalation valve connecting the first volume and the second volume; and
    a one-way exhalation valve located within a wall of the outer housing, the exhalation valve connecting the second volume and an exterior of the outer housing,
    wherein, in an expanded state, gas is flowable from the connected MDI to the first volume, from the first volume to the second volume, and from the second volume to the mouth of a user.

2. The apparatus of claim 1, wherein the outer housing and the inner flap are constructed from a single piece of stock.

3. The apparatus of claim 2, wherein the inner flap is connected to the outer housing at a fold.

4. The apparatus of claim 2, wherein the single piece is sheet stock, and wherein the outer housing and the inner flap are formed by folding the sheet.

5. The apparatus of claim 4, wherein the outer housing is connected to the inner flap adjacent a mouth opening side of the sheet stock.

6. The apparatus of claim 1, wherein the outer housing and an inner housing are at least partially constructed from antistatic material.

7. The apparatus of claim 1, wherein the inner flap is adhesively attached to a bottom panel of the outer housing along at least three adhesive lines arranged in an "H" pattern.

8. The apparatus of claim 1, wherein the inner flap comprises an adhesive panel adjacent to a top panel of the outer housing, and wherein the adhesive panel is adhesively attached to the top panel of the outer housing.

9. The apparatus of claim 8, wherein the adhesive panel extends substantially across a width of the inner flap.

10. A medication inhalation apparatus, comprising:
    an outer housing, collapsible into a substantially flat configuration and expandable to bound a first volume adapted to receive a plume of medication particles ejected by an MDI (metered dose inhaler);
    an inner flap located within the outer housing and expandable to bound a second volume within the outer housing, wherein an edge panel of the inner flap is affixed to a portion of the outer housing to secure the second volume, wherein the inner flap includes first, second, third, fourth and fifth panels connected to one another along straight scored fold lines;
    a pair of side panels connected to the second and third panels along further straight fold lines;
    a first opening formed through a wall of the outer housing at a first location, in fluid communication with the first volume, and adapted to accommodate a mouthpiece of the MDI;
    a second opening formed through a wall of an outer panel of the inner flap, and adapted to form a user mouth opening in fluid communication with the second volume;
    a one-way inhalation valve located within a central panel of the inner flap, the inhalation valve connecting the first volume and the second volume; and
    a one-way exhalation valve located within an outer panel of the inner flap in a second location and a wall of the outer housing, the exhalation valve connecting the second volume and an exterior of the outer housing,
    wherein, in an expanded state, gas is flowable from the connected MDI to the first volume, from the first volume to the second volume, and from the second volume to the mouth of a user.

11. The apparatus of claim 10, wherein the outer housing and the inner flap are constructed from a single piece of stock.

12. The apparatus of claim 11, wherein the inner flap is connected to the outer housing at a fold.

13. The apparatus of claim 11, wherein the single piece is sheet stock, and wherein the outer housing and the inner flap are formed by folding the sheet.

14. The apparatus of claim 13, wherein the outer housing is connected to the inner flap adjacent a mouth opening side of the sheet stock.

15. The apparatus of claim 10, wherein the outer housing and an inner housing are at least partially constructed from antistatic material.

16. The apparatus of claim 10, wherein the one-way exhalation valve comprises an exhalation valve located within the inner flap and a valve opening located within a wall of the outer housing.

17. A method of expanding a medication inhalation apparatus from an initially flat, collapsed state, to an expanded state comprising the steps of:

providing, in the collapsed state, an outer housing, an inner flap located within the outer housing, wherein the outer housing and the inner flap are substantially airtight when expanded, wherein the inner flap includes first, second, third, fourth and fifth panels connected to one another along straight fold lines, and a pair of side panels connected to the second and third panels along further straight fold lines;

an inhaler opening formed at least partially within a sidewall of the outer housing at a first location, a mouth opening positioned within a sidewall of the outer housing at a second location, a one-way inhalation valve positioned within a sidewall of the inner flap, and a one-way exhalation valve positioned within a sidewall of the outer housing at a third location;

pressing a pair of opposite sidewall panels on the outer housing; and manually expanding the outer housing and inner flap to create a first volume encompassed by the outer housing and a second volume encompassed by the inner flap and the outer housing, wherein the inhaler opening is in fluid communication with the first volume, wherein the mouth opening is in fluid communication with the second volume, wherein the inhalation valve connects the first volume and the second volume, wherein the exhalation valve connects the second volume and an exterior of the outer housing, and wherein gas is flowable from the inhaler to the first volume, from the first volume to the second volume, and from the second volume to the mouth of a patient.

* * * * *